United States Patent
Reddy et al.

(10) Patent No.: US 8,115,004 B2
(45) Date of Patent: Feb. 14, 2012

(54) PROCESS FOR PURE MONTELUKAST SODIUM THROUGH PURE INTERMEDIATES AS WELL AS AMINE SALTS

(75) Inventors: Manne Satyanarayana Reddy, Hyderabad (IN); Muppa Kishore Kumar, Hyderabad (IN); Karamala Rama Subba Reddy, Kadapa (IN); Durgadas Shyla Prasad, Hyderabad (IN)

(73) Assignee: MSN Laboratories Limited, Hyderabad, Andhra Pradesh (IN)

( * ) Notice: Subject to any disclaimer, the term of this patent is extended or adjusted under 35 U.S.C. 154(b) by 250 days.

(21) Appl. No.: 12/312,660

(22) PCT Filed: Nov. 19, 2007

(86) PCT No.: PCT/IN2007/000542
§ 371 (c)(1),
(2), (4) Date: Jul. 10, 2009

(87) PCT Pub. No.: WO2008/062478
PCT Pub. Date: May 29, 2008

(65) Prior Publication Data
US 2010/0056793 A1    Mar. 4, 2010

(30) Foreign Application Priority Data
Nov. 20, 2006  (IN) .......................... 2152/CHE/2006
May 9, 2007    (IN) ............................. 979/CHE/2007

(51) Int. Cl.
C07D 215/14    (2006.01)
(52) U.S. Cl. ..................................................... 546/174
(58) Field of Classification Search .................. None
See application file for complete search history.

(56) References Cited

U.S. PATENT DOCUMENTS

| | | | |
|---|---|---|---|
| 5,565,473 | A | 10/1996 | Belley et al. |
| 5,614,632 | A | 3/1997 | Bhupathy et al. |
| 2005/0107426 | A1 | 5/2005 | Overeem et al. |
| 2005/0107612 | A1 | 5/2005 | Reguri et al. |
| 2005/0234241 | A1 | 10/2005 | Sundaram et al. |
| 2006/0194838 | A1 | 8/2006 | Chou et al. |
| 2007/0078158 | A1 | 4/2007 | Sterimbaum et al. |
| 2009/0171092 | A1 | 7/2009 | Reddy et al. |

FOREIGN PATENT DOCUMENTS

| | | |
|---|---|---|
| EP | 0 480 717 B1 | 4/1998 |
| WO | WO 2004/108679 A1 | 12/2004 |
| WO | WO 2006/058545 A1 | 6/2006 |
| WO | WO 2007/004237 A2 | 1/2007 |
| WO | WO 2007/069261 | 6/2007 |
| WO | WO 2007/069261 A1 | 6/2007 |
| WO | WO 2007/116240 A1 | 10/2007 |
| WO | WO 2008/062478 A2 | 5/2008 |

OTHER PUBLICATIONS

International Search Report for Int'l Application No. PCT/IN2007/000542; Date Mailed: Dec. 3, 2009.
Dufresne, C., et al, "Synthesis of Montelukast (MK-0476) Metabolic Oxidation Products," *J. Org. Chem.*, 61: 8518-8525 (1996).
Written Opinion of the International Searching Authority for PCT/IN2007/000542, Date of Mailing Dec. 3, 2008, 8 pp.
International Preliminary Examination Report for PCT/IN 2007/000542, Date of completion of report Aug. 3, 2010, 14 pp.
International Search Report for Int'l Application No. PCT/IN2006/000086, Date Mailed: Sep. 25, 2006, 2 pages.
International Preliminary Examination Report for Int'l Application No. PCT/IN2006/000086, Date of Completion of Report: Jun. 13, 2008, 10 pages.
Written Opinion for PCT/IN2006/000086, Date Mailed: Sep. 25, 2006, 3 pages.
Non-Final Office Action for U.S. Appl. No. 12/086,436 dated Sep. 6, 2011.

*Primary Examiner* — Janet L. Andres
*Assistant Examiner* — Timothy R Rozof
(74) *Attorney, Agent, or Firm* — Hamilton, Brook, Smith & Reynolds, P.C.

(57) ABSTRACT

The present invention provides an improved process for the preparation of highly pure montelukast sodium through highly pure diol intermediate compound of formula (2) and (1)-(mercapto methyl)cyclopropane acetic acid methyl ester compound of formula (4) or mercaptomethyl cyclopropane acetic acid compound of formula (7). The present invention also provides novel organic amine salts of montelukast.

8 Claims, 7 Drawing Sheets

PROCESS FOR PURE MONTELUKAST SODIUM THROUGH PURE INTERMEDIATES AS WELL AS AMINE SALTS

RELATED APPLICATIONS

This application is the U.S. National Stage of International Application No. PCT/IN2007/000542, filed Nov. 19, 2007, which designates the U.S., published in English, and claims priority under 35 U.S.C. §§ 119 or 365(c) to Indian Application No. 2152/CHE/2006, filed Nov. 20, 2006 and to Indian Application No. 979/CHE/2007, filed May 9, 2007. The entire teachings of the above applications are incorporated herein by reference.

FIELD OF THE INVENTION

The present invention relates to an improved process for the preparation of highly pure montelukast sodium compound of formula-1,

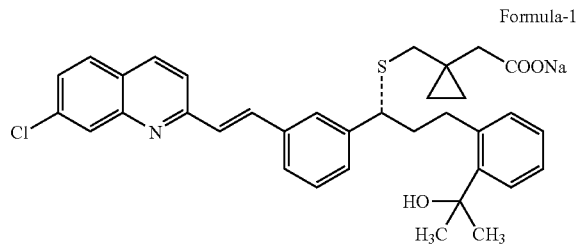

Formula-1 through highly pure intermediate compounds of formula-2 and formula-4 or formula-7

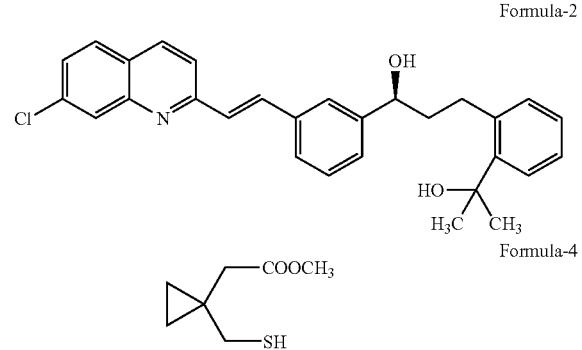

Formula-2

Formula-4 as well as through novel organic amine salt of montelukast compound of formula-5,

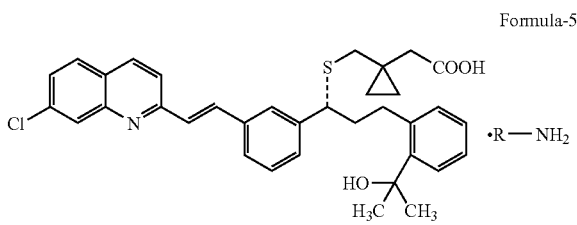

Formula-5

Furthermore, the present invention relates to an improved process for the preparation of highly pure diol compound of formula-2 and process for the purification of mercaptomethyl cyclopropane acetic acid compound of formula-7.

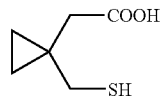

Formula-7

Montelukast sodium is a leukotriene D4 antagonist. Montelukast sodium is indicated for the prophylaxis and chronic treatment of asthma in adults and pediatric patients. It is also indicated for the relief of symptoms of seasonal allergic rhinitis and for perennial allergic rhinitis in adults and pediatric patients. Montelukast sodium salt is available in a number of oral formulations including tablets, chewable tablets and oral granules.

BACKGROUND OF THE INVENTION

EP 480717 discloses a process for the synthesis of montelukast and its pharmaceutically acceptable salts especially sodium salt. The process for the preparation comprises of reacting [(E)]-2-(2-(2-(3(S)-(3-(2-(7-chloro-2-quinolinyl)ethenyl)phenyl)-3-(methanesulfonyloxy)propyl)phenyl)-2-propoxy) tetrahydropyran with methyl 1-(acetyl thiomethyl) cyclopropane acetate in presence of hydrazine, cesium carbonate in acetonitrile as a solvent to get methyl ester of montelukast in pyran protected form. The protected compound is further reacted with pyridinium p-toluene sulfonate, sodium hydroxide in a mixture of methanol and tetrahydrofuran as a solvent to afford montelukast sodium.

The drawback of this process is that, it involves more number of steps, which includes series of protection and de-protection of diol intermediate, usage of hazardous and costly raw materials such as hydrazine, pyridinium p-toluenesulonate in typical reaction conditions i.e., at very low temperatures. Hence is not suitable for commercial scale-up.

U.S. Pat. No. 5,614,632 disclose a process for the preparation of 1-(mercapto methyl)cyclopropane acetic acid, which is a key intermediate for the preparation of montelukast sodium. The said patent claimed an improved process for the preparation of montelukast sodium including the process for the preparation of its key intermediates. The drawback of this process is that, it involves the usage of pyrophoric and costly raw material such as n-butyl lithium in typical reaction conditions i.e., at very low temperatures. The processes also involves tedious workup to isolate the required product and thus results in the excess time cycle, which in turn renders the process more costly and less eco friendly thus the process is not suitable for commercial scale-up.

The styrene impurity and sulfoxide impurity (Impurity-E) of montelukast sodium were first disclosed in J. Org. Chem. 61, 8518-8525, 1996. This journal also disclosed the pathways for the formation of styrene and sulfoxide impurity.

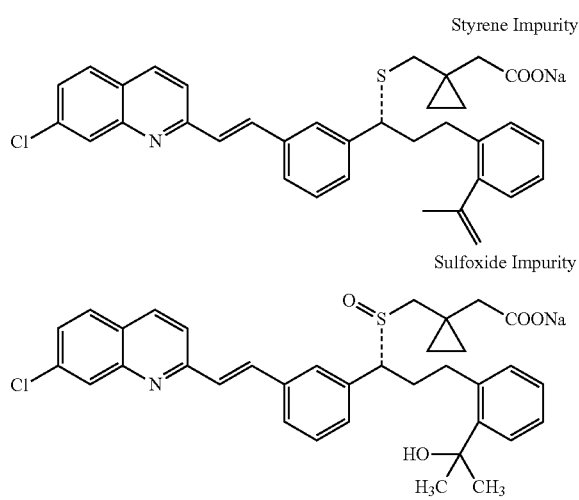

Styrene Impurity

Sulfoxide Impurity

As per the disclosed process styrene impurity was formed due to the dehydration of tertiary alcohol of montelukast when the reaction was performed in acidic media and the sulfoxide impurity is formed due to aerial oxidation of montelukast.

The purity of montelukast sodium obtained as per the prior art process is not satisfactory and for this reason a series of purification steps are required to provide a product which meets the quality requirement of pharmaceutical active ingredients.

Generally any synthetic compounds or for example montelukast sodium can contain extraneous compounds or impurities that can be derived from many sources. It is known from the art that impurities in an any API may arise from degradation of API itself, which is related to the stability of the API during storage, and the manufacturing process, including the chemical synthesis. Process impurities include unreacted starting materials, chemical derivatives of impurities contained in starting materials, synthetic by-products, and degradation products.

Montelukast sodium prepared as per the prior art process has five major impurities along with the unreacted starting material. The impurities which are present in montelukast sodium are designated as Impurities A, B, C, D and E. The corresponding derivatives or origin of the impurities A, B, C and D are designated as A*, B*, C* and D* respectively, which are present in the starting material compound of formula-2. The structural formulas of impurities A, B, C and D and their corresponding derivatives A*, B*, C*, D* as well as the impurity E are represented as below.

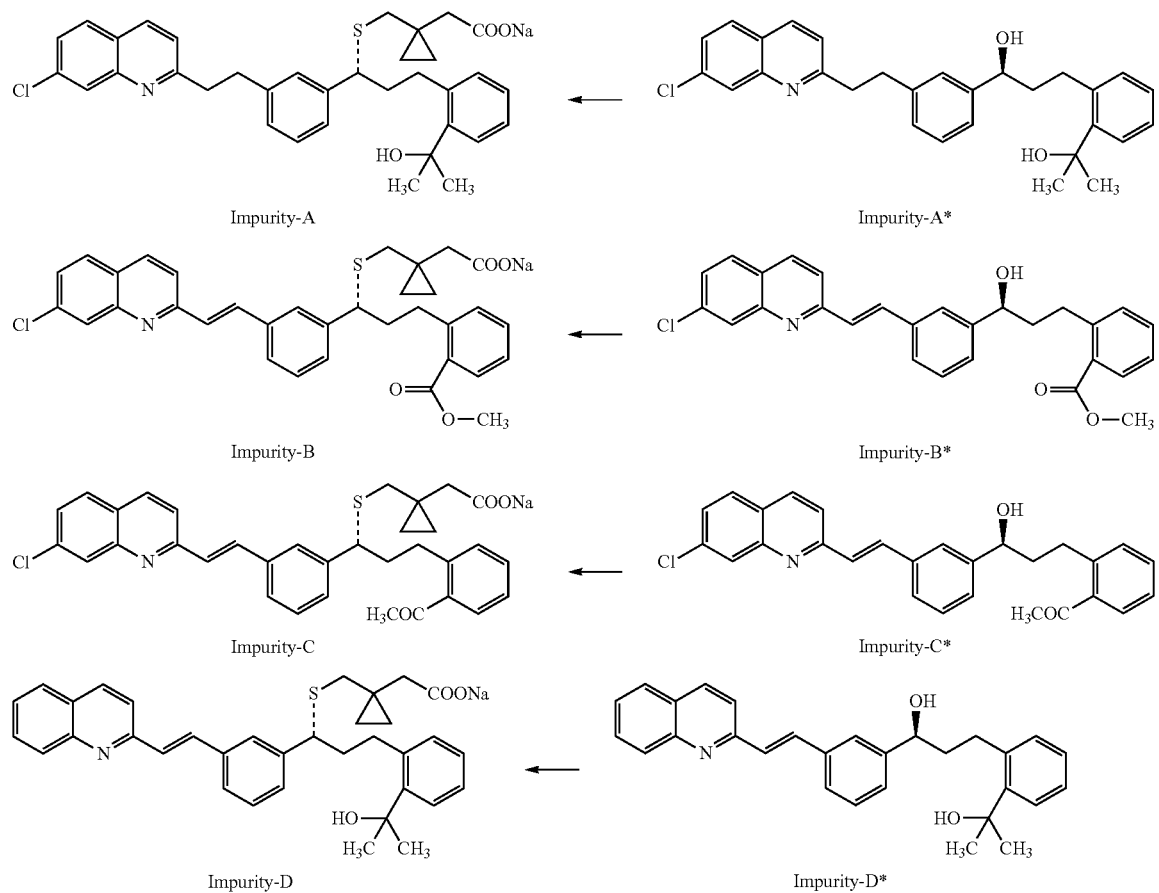

Impurity-A

Impurity-A*

Impurity-B

Impurity-B*

Impurity-C

Impurity-C*

Impurity-D

Impurity-D*

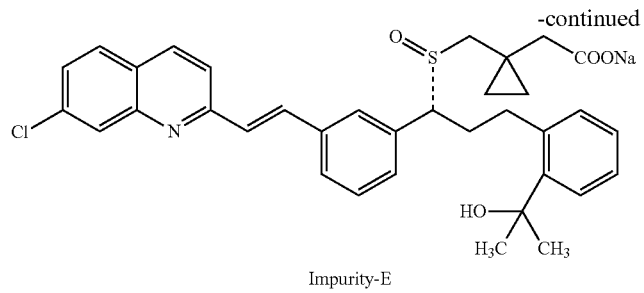

Impurity-E

Apart from the above mentioned impurities, the dimer impurities such as diacid impurity as well as its corresponding salts have been observed in montelukast sodium. The dimer impurities are derived from the mercaptomethyl cyclopropane acetic acid intermediate compound of formula-7. The dimer impurities such as diacid and diester having the following structural formula.

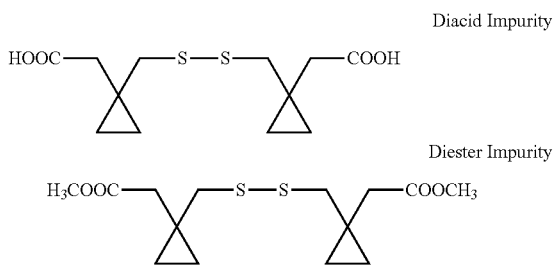

Impurities in montelukast sodium or any active pharmaceutical ingredient are undesirable and, in extreme cases, might even be harmful to a patient being treated with a dosage form containing that active pharmaceutical ingredient. So it is important to reduce the impurities to meet the quality requirement of pharmaceutical active ingredients.

In order to reduce the above mentioned impurities in the montelukast sodium, the prior art methods teaches three ways of purification, those are purification of montelukast sodium or purification of montelukast organic amine salts followed by conversion of amine salts into sodium salt or by the purification of montelukast free acid. All the prior art methods involves repeated purifications at final or pre final stage without mentioning the origin/cause of the impurities. Generally repeated purifications at the final stage of any compound will lead to loss of material which increases the cost of production.

The aim of the present invention is to provide an improved process for the preparation of pure montelukast sodium through highly pure intermediate compounds free from corresponding derivatives of impurities A, B, C & D, as well as free from diacid and diester impurities.

We the present inventors found that the origin of impurities A, B, C and D which were observed in the montelukast sodium was due to the carryover of corresponding derivatives present in the starting material (i.e., compound of formula-2) and the impurity-E was observed due to an aerial oxidation of montelukast. The present invention eliminates the corresponding derivatives of so called impurities (i.e., A, B, C, D, diacid and diester impurities) present in the starting materials, by purification of the starting material (i.e., at the point of origin of impurities) which will avoids the loss of material caused by the purification in the final step as disclosed in prior art. The usage of starting materials which are free from corresponding derivatives of above said impurities leads to the highly pure montelukast sodium.

Further more the main drawback of the prior art processes is that, the removal of dicylcohexyl amine salt from the montelukast or its pharmaceutically acceptable salts requires number of purifications, which makes the process tedious. Dicyclohexylamine traces still contaminates with the montelukast or its pharmaceutically acceptable salts even after repeated purifications, thereby limiting the scope for achieving high purity and industrial applicability.

So it was the aim of the present inventors to develop a novel organic amine salts of montelukast which possessing high advantageous physico-chemical properties, high degree of crystallinity and thermodynamic stability and easily removed from the reaction mixture or from the final product by simple washing or by simple purification methods which gives the montelukast or its pharmaceutically acceptable salts free from organic amine salt traces.

In general alkali salts of any API possesses hygroscopic nature, for example montelukast sodium is highly hygroscopic in nature so it cannot be dried in a tray drier in normal atmospheric conditions as it liquefies by exposing to the atmosphere. Hence it is required to dry the material in a tray drier under specific controlled environment to control the hygroscopic nature of montelukast sodium. There is a need in the art to develop a tray drying techniques which avoids the above problems.

The patent publication US 2006/194838 discloses the needle shaped morphology of montelukast sodium which is difficult to formulate. The present inventors provide a process for the preparation of montelukast sodium in non-needle shaped morphology which is easy to formulate.

Another aspect of the present invention is to provide an improved process for the preparation of highly pure intermediate compound of formula-2.

Another aspect of the present invention is to provide a process for purification of mercaptomethyl cyclopropane acetic acid compound of formula-7.

The improved process for the preparation highly pure montelukast sodium provided by the present invention is cost effective as well as the obtained montelukast sodium is highly pure and suitable for pharmaceutical compositions.

BRIEF DESCRIPTION OF THE INVENTION

Accordingly, the first aspect of the present invention provides an improved process for the preparation of highly pure montelukast sodium compound of formula-1 through highly pure intermediate compounds and novel organic amine salts,

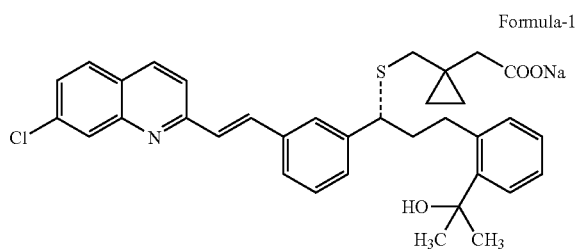

Formula-1 which comprises of the following steps:
a) reacting the pure diol compound of formula-2 free from corresponding derivatives of impurities A, B, C and D with methane sulphonyl chloride in presence of a suitable organic solvent or mixture of solvents to give methane sulfonate compound of formula-3, which on reacting in-situ with pure 1-(mercapto methyl)cyclopropane acetic acid methyl ester compound of formula-4 free from diacid and diester impurities, in presence of polar aprotic solvent with or without combination of $C_1$-$C_4$ alcohol in presence of a strong base like alkali or alkaline earth metal alkoxide, followed by treating the obtained compound with organic amine salt in a suitable keto or ester solvents provides corresponding montelukast organic amine salt compound of formula-5,
b) optionally purifying the montelukast organic amine salt compound of formula-5 using hydrocarbon solvents or keto solvents or mixtures thereof,
c) converting the montelukast organic amine salt compound of formula-5 into its sodium salt compound of formula-1 by treating with sodium source in a suitable solvent, without going through montelukast free acid.

The preparation of montelukast sodium in step c) without going through montelukast free acid by the displacement of weak base (organic amine) by a strong base (sodium ion source) which avoids the tedious workup process there by avoiding the aerial exposure of montelukast, which controls the formation of sulfoxide impurity as well as Cis-isomer impurity.

The second aspect of the present invention provides an improved process for the preparation of pure diol compound of formula-2 free from corresponding derivatives of impurities A, B, C and D,

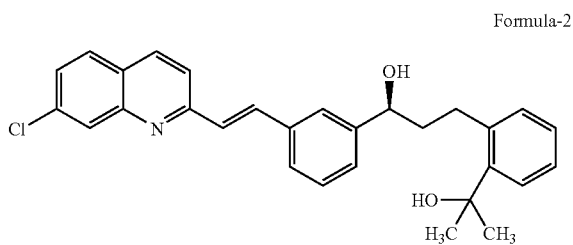

Formula-2 which comprises of the following steps:
a) reacting the benzoate compound of formula-6 with grignard reagent in a suitable organic solvent with the combination of chloro solvents as a co-solvent to give diol compound of formula-2,
b) purifying the diol compound of formula-2 in a suitable organic solvent to give pure diol compound of formula-2 free from the corresponding derivatives of impurities A, B, C and D.

The third aspect of the present invention provides a process for the purification of mercaptomethyl cyclopropane acetic acid compound of formula-7 to provide the pure mercaptomethyl cyclopropane acetic acid compound of formula-7 free from the diacid impurity,

Formula-7

Which comprises of the following steps:
a) dissolving the mercaptomethyl cyclopropane acetic acid compound of formula-7 in a suitable organic solvent,
b) cooling the above obtained solution to 0° C.,
c) separating the precipitated diacid impurity by filtration,

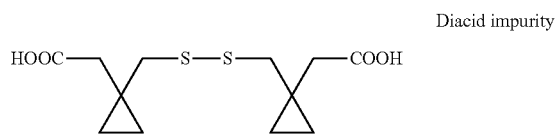

Diacid impurity d) concentrating the filtrate to provide pure mercaptomethyl cyclopropane acetic acid compound of formula-7 free from the diacid impurity.

The pure compound of formula-7 free from the diacid impurity obtained as per the third aspect of the present invention is converted into pure 1-(mercapto methyl)cyclopropane acetic acid methyl ester compound of formula-4 free from diacid and diester impurities by conventional methods.

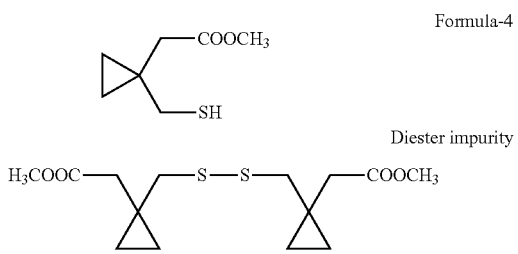

Formula-4

Diester impurity

The fourth aspect of the present invention provides novel organic amine salts of montelukast compound of formula-5,

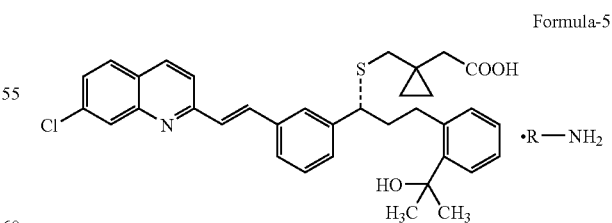

Formula-5

The novel organic amine salts selected from n-butyl amine, isobutyl amine and (+/−)-sec-butyl amine. The novel amine salts of montelukast are readily isolable in a substantially crystalline form and are used for the preparation of pure montelukast or its pharmaceutically acceptable salts like sodium.

The fifth aspect of the present invention provides a process for the preparation of novel organic amine salt of montelukast compound of formula-5, Formula-5

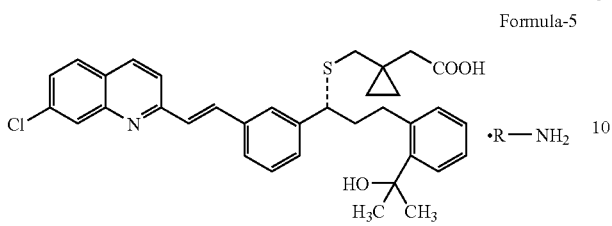

which comprises of reacting the pure diol compound of formula-2 with methane sulphonyl chloride in presence of a suitable organic solvent or mixture of solvents to give methane sulfonate compound of formula-3, which on reacting in-situ with pure 1-(mercapto methyl)cyclopropane acetic acid methyl ester compound of formula-4 in presence of polar aprotic solvent with or without combination of $C_1$-$C_4$ alcohol in presence of a strong base like alkali or alkaline earth metal alkoxide, followed by treating the obtained compound with suitable organic amine like n-butyl amine, isobutyl amine and (+/−)-sec-butyl amine in a suitable non-polar organic solvents and/or keto solvents and/or ester solvents followed by optional seeding with the corresponding organic amine salt of montelukast compound gives corresponding montelukast organic amine salt compound of formula-5 and optionally purifying the montelukast organic amine salt compound of formula-5 using suitable solvent.

The sixth aspect of the present invention provides the use of novel organic amine salts of montelukast in the preparation of highly pure montelukast or its pharmaceutically acceptable salts. The process for the preparation of pure montelukast or its pharmaceutically acceptable salts comprises of treating the novel organic amine salt like n-butyl amine, isobutyl amine and sec-butyl amine of montelukast compound of formula-5 of the present invention with sodium source in a suitable solvent.

The seventh aspect of the present invention provides a drying process for amorphous montelukast sodium.

ADVANTAGES OF THE PRESENT INVENTION

Provides an improved process for the preparation of highly pure montelukast sodium through highly pure diol compound of formula-2 free from the corresponding derivatives of impurities A, B, C and D; pure 1-(mercapto methyl)cyclopropane acetic acid methyl ester compound of formula-4 free from the diacid and diester impurities, as well as through novel organic amine salts.

Controlling the impurities A, B, C and D of montelukast sodium by eliminating the corresponding derivatives in the starting material compound of formula-2 (i.e., at the point of origin of impurity) itself by simple purification of diol compound of formula-2.

Reducing the diacid impurity present in the mercaptomethyl cyclopropane acetic acid compound of formula-7 by employing simple purification method.

Converting the pure mercaptomethyl cyclopropane acetic acid compound of formula-7 free from diacid impurity into pure 1-(mercapto methyl)cyclopropane acetic acid methyl ester compound of formula-4 and thereby controlling the formation of diester impurity.

Provides novel organic amine salts of monteluakst like n-butylamine, isobutylamine and sec-butylamine.

Avoiding the final stage purification and there by reducing the cost of production, waste of material and solvent by employing the purification at the initial stages as mentioned above.

The n-butyl amine salt of montelukast is free flow solid which is easy to handle in further reactions and the traces are easily removable from the final products.

Highest yield and purity obtained in the preparation of compound of formula-2 by using chloro solvent as a co-solvent in grignard reaction.

Preparation of montelukast sodium without going through montelukast free acid by the displacement of weak base (organic amine) by a strong base (sodium ion source) there by avoiding the aerial exposure of montelukast, which controls the formation of sulfoxide impurity as well as Cis-isomer impurity.

Preparation of montelukast sodium without going through montelukast free acid avoids the tedious workup process which causes the formation of sulfoxide, Cis-isomer impurities and thereby reducing the cycle-time of the reaction and effluent load.

Environment friendly and cost-effective process

BRIEF DESCRIPTION OF THE DRAWINGS

FIG. 5: Illustrates the GC chromatogram of compound of formula-7.

DETAILED DESCRIPTION OF THE PRESENT INVENTION

Figure 1:
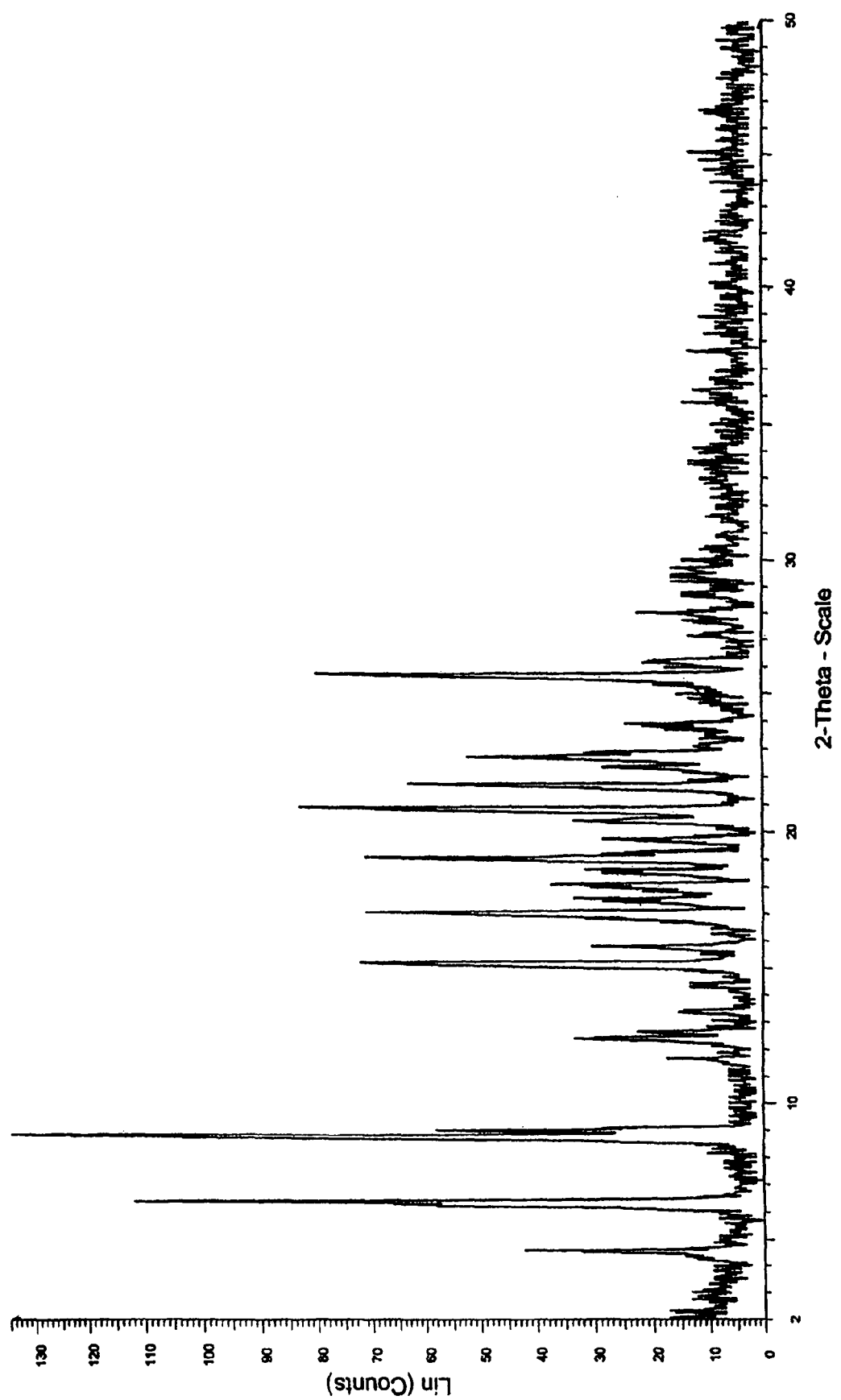
FIG. 1: Illustrates the powder X-ray diffraction pattern of n-butyl amine salt of montelukast.

The present invention relates to an improved process for the preparation of highly pure montelukast sodium through pure intermediates as well as novel organic amine salts. Montelukast sodium is chemically known as sodium salt of 1-[[[(1R)-1-[3-[(1E)-2-(7-chloro-2-quinolinyl)ethenyl]phenyl]-3-[2-(1-hydroxy-1-methylethyl)phenyl]propyl]thio]methyl]cyclopropaneacetic acid represented by the compound of formula-1.

Formula-1

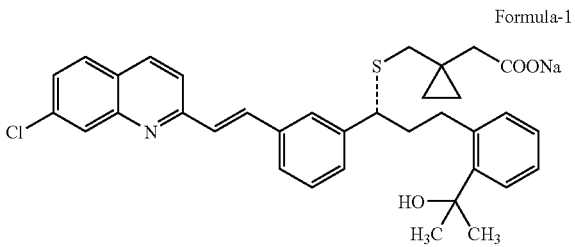

The first aspect of the present invention is to provide an improved process for the preparation of highly pure montelukast sodium compound of formula-1 through pure intermediate compound of formula-2 free from corresponding derivatives of impurities A, B, C and D and 1-(mercaptomethyl)cyclopropane acetic acid methyl ester compound of formula-4 free from diacid and diester impurities as well as through novel organic amine salts of montelukast, which comprises of the following steps:

a) reacting the pure diol compound of formula-2 free from the corresponding derivatives of impurities A, B, C and D, Formula-2

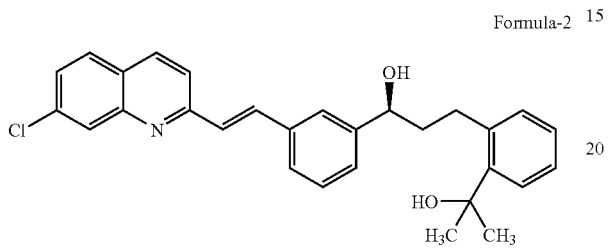

with methane sulphonyl chloride in a suitable organic solvent like toluene and acetonitrile in a suitable amine base like diisopropylethylamine to give the compound of formula-3, Formula-3

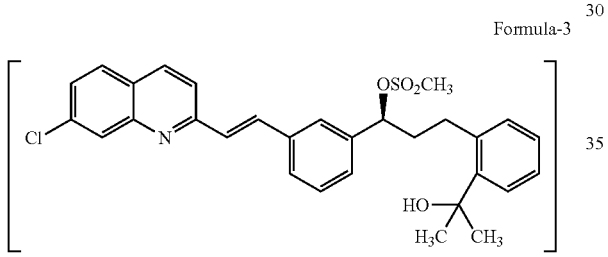

which on reacting in-situ with pure 1-(mercaptomethyl)cyclopropane acetic acid methyl ester compound of formula-4 free from the diacid and diester impurities, Formula-4

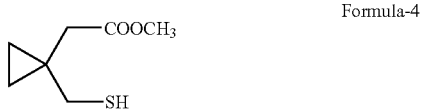

in presence of polar aprotic solvent like dimethylsulfoxide, dimethyl acetamide with or without combination of $C_1$-$C_4$ alcoholic solvents like methanol, ethanol, propanol, butanol, and strong base like alkali or alkaline earth metal alkoxides i.e., potassium tertiary butoxide, sodium methoxide, sodium ethoxide, preferably sodium methoxide in DMSO (dimethylsulfoxide) at a temperature of −20 to 0° C. for 5 to 20 hours, preferably at a temperature of about −5 to 5° C. for 8-10 hours, b) quenching the reaction mixture with aqueous sodium hydroxide solution, then extracting with water immiscible solvents like hydrocarbon solvents, chloro solvents, ester solvents, preferably hydrocarbon solvents more preferably toluene, c) lowering pH of the reaction mixture with acetic acid then extracting the montelukast with ester solvents, chloro solvents, preferably ester solvents more preferably ethyl acetate followed by concentrating the solvent and then dissolving the obtained residue in a suitable solvent selected from keto solvents like acetone, butanone or ester solvents like ethyl acetate, propyl acetate, preferably acetone and ethyl acetate, d) treating the product obtained from step c. with an organic amine such as organic amine like cyclic amines such as cyclopropyl amine, cyclo pentyl amine, cyclo hexyl amine, pyrrolidine or morpholine or alkyl amines such as methyl amine, isopropyl amine, disiopropyl amine, tert-butyl amine, n-butylamine, sec-butyl amine, iso-butyl amine, n-octyl glucamine or aryl amines such as phenyl ethyl amine, phenyl propyl amine preferably tertiary butyl amine in a suitable solvent selected from keto solvents like acetone, butanone or ester solvents like ethyl acetate, propyl acetate, preferably acetone and ethyl acetate at a temperature of 20-40° C. for 5-15 hours, preferably at a temperature of about 25-35° C. for 8-10 hours under inert atmosphere to give corresponding montelukast organic amine salt compound of formula-5, Formula-5

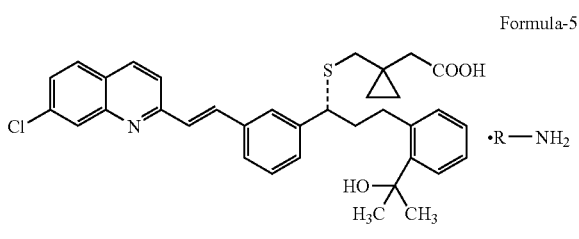

e) optionally purifying the montelukast organic amine salt compound of formula-5 using hydrocarbon solvents like toluene, hexanes, heptane or keto solvents like acetone or mixtures thereof, f) treating the corresponding organic amine salt of montelukast compound of formula-5 with sodium ion source like sodium hydroxide, sodium methoxide preferably sodium hydroxide in methanol at a temperature of 0-40° C. for 15 to 90 minutes, preferably at a temperature of 5-15° C. for 45 minutes under inert atmosphere, followed by distillation of methanol and organic amine to get the sodium salt of montelukast, which is then dissolved in a suitable solvent like toluene and saturated the toluene layer with a solvent selected from cyclohexane, hexane and heptane preferably heptane gives montelukast sodium compound of formula-1.

Preparation of montelukast sodium without going through montelukast free acid by the displacement of weak base (organic amine) by a strong base (sodium ion source) there by avoiding the tedious work up process thereby avoiding the aerial exposure of montelukast, which controls the formation of sulfoxide impurity as well as Cis-isomer impurity having the following structural formula.

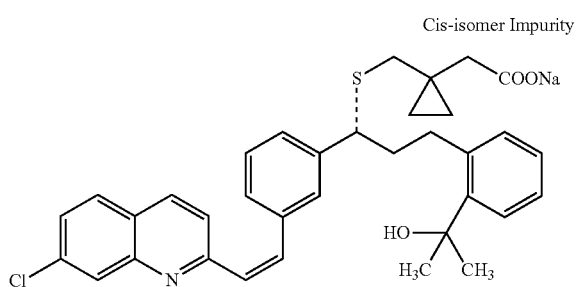

Cis-isomer Impurity

The second aspect of the present invention is to provide an improved process for the preparation of pure diol compound of formula-2 free from the corresponding derivatives of impurities A, B, C and D,

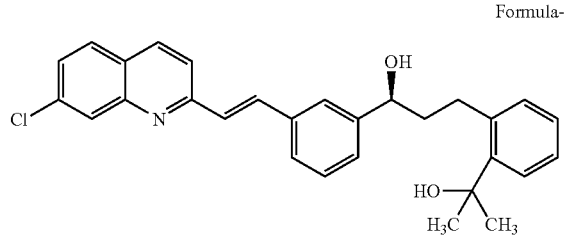

Formula-2

Which comprises of the following steps;
a) reacting the benzoate compound of formula-6

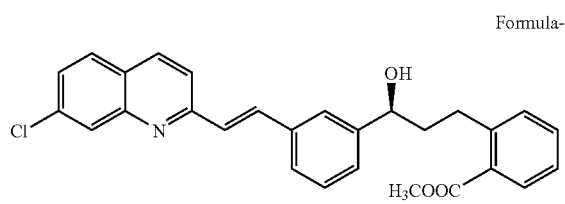

Formula-6 with grignard reagent such as methyl magnesium chloride or methyl magnesium bromide preferably methyl magnesium chloride in a solvent like tetrahydrofuran and/or toluene in combination of co-solvent such as chloro solvents like methylene chloride, chloroform and ethylene chloride preferably methylene chloride to provide the diol compound of formula-2, b) purifying the diol compound of formula-2 with a suitable organic solvents like toluene, heptane, hexanes and cyclohexane to provide the pure diol compound of formula-2 free from the corresponding derivatives of impurities like A, B, C and D.

The third aspect of the present invention is to provide a process for the purification of mercaptomethyl cyclopropane acetic acid compound of formula-7,

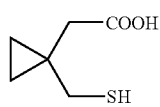

Formula-7 which comprises of the following steps:

a) dissolving the mercaptomethyl cyclopropane acetic acid compound of formula-7 in a suitable organic solvents like toluene, heptanes and hexanes,
b) cooling the above obtained solution to 0° C.,
c) separating the precipitated diacid impurity compound by filtration,

Diacid impurity d) concentrating the filtrate to get pure mercaptomethyl cyclopropane acetic acid compound of formula-7 free from the diacid impurity.

The pure mercaptomethyl cyclopropane acetic acid compound of formula-7 free from the diacid impurity is converted into pure 1-(mercaptomethyl)cyclopropane methyl ester compound of formula-4 free from the diacid and diester impurity by conventional methods.

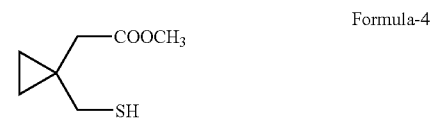

Formula-4

The usage of mercaptomethyl cyclopropane acetic acid compound of formula-7 free from diacid impurity in the preparation of 1-(mercaptomethyl)cyclopropane acetic acid methyl ester compound of formula-4 controls the formation of diester impurity in the 1-(mercaptomethyl)cyclopropane methyl ester compound of formula-4 and the same which is used for the preparation of montelukast sodium leads to highly pure montelukast sodium free from diacid and its corresponding salts.

The fourth aspect of the present invention is to provide a novel organic amine salt of montelukast compound of formula-5,

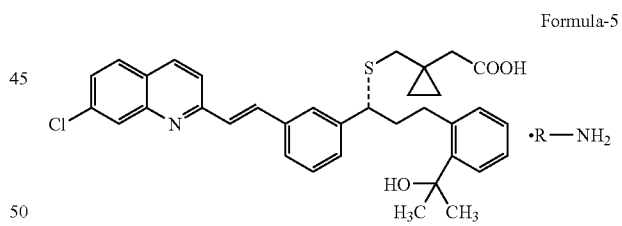

Formula-5

The preferable novel organic amine salts are n-butyl amine, isobutyl amine and (+/−)-sec-butyl amine of montelukast, which can be easily isolated from the reaction mixture in crystalline form, and then, if necessary, purified by recrystallisation from typical organic solvents to reduce the impurities to acceptable level. The novel organic amine salt of montelukast easily converted into pure montelukast or its pharmaceutically acceptable salts, for example sodium salt.

Figure 2:
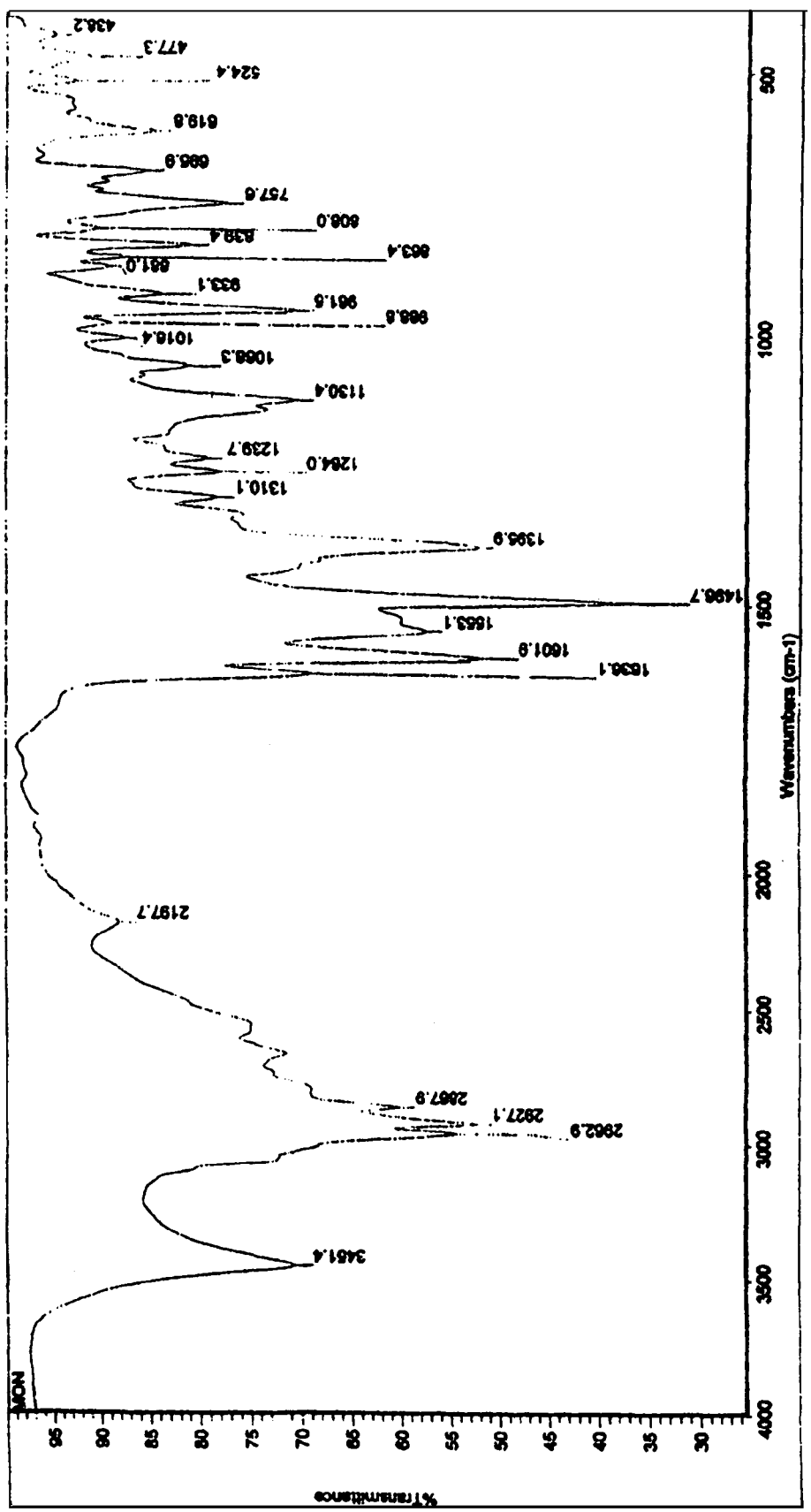
FIG. 2: Illustrates the IR spectrum of n-butyl amine salt of montelukast.
Figure 3:
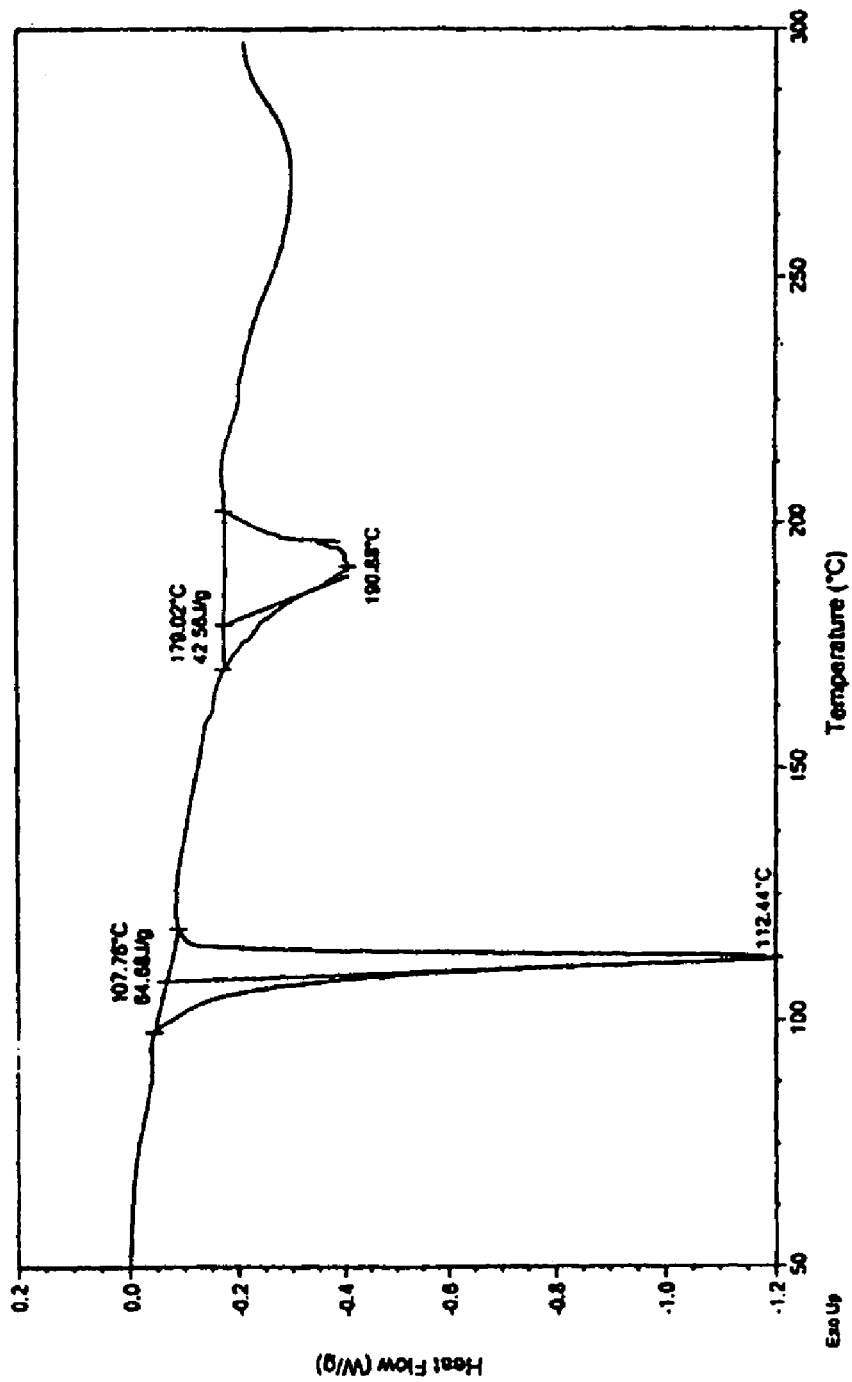
FIG. 3: Illustrates the DSC thermo gram of n-butyl amine salt of montelukast.
Figure 4:
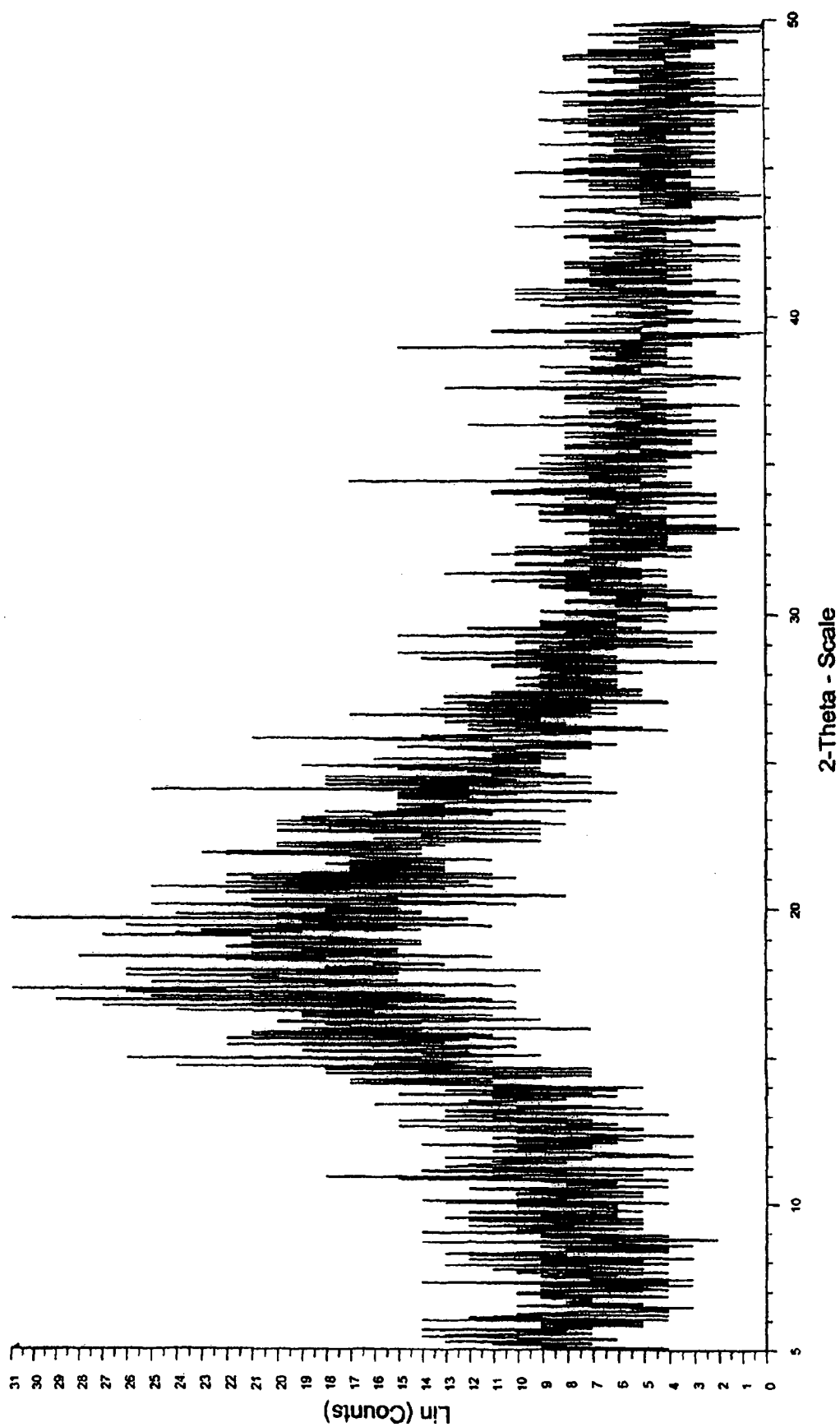
FIG. 4: Illustrates the powder X-ray diffraction pattern of amorphous montelukast sodium.

The n-butyl amine salt of montelukast is characterized by X-ray powder diffraction pattern having peaks at about 6.2, 8.6, 8.9, 15.0, 16.9, 18.9, 20.7, 22.6, 25.5 and 29.9 degrees two-theta±0.2 degrees two-theta The n-butyl amine salt of montelukast is characterized by its X-ray powder diffraction pattern substantially as shown in FIG. 1, IR spectrum as shown in FIG. 2 and DSC thermogram as shown in FIG. 3.

The n-butylamine salt of montelukast of the present invention is possessing high advantageous physico-chemical properties, high degree of crystallinity, free flow solid and thermodynamic stability and easily removed from the reaction mixture or from the final product by simple washing or by simple purification methods which gives the montelukast or its pharmaceutically acceptable salts free from organic amine salt traces.

The fifth aspect of the present invention is to provide a process for the preparation of novel organic amine salt of montelukast compound of formula-5,

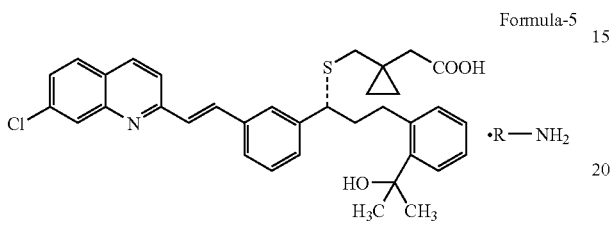

Formula-5 which comprises of the following steps;
a) reacting the pure diol compound of formula-2

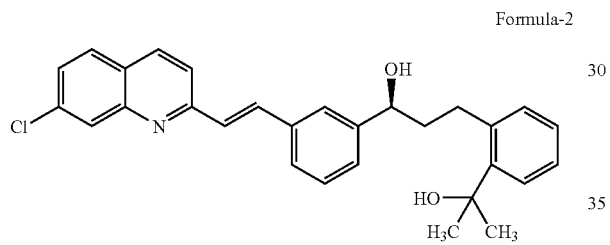

Formula-2 with methane sulphonyl chloride in a suitable organic solvent like toluene and acetonitrile in a suitable amine base like diisopropylethylamine to give the compound of formula-3,

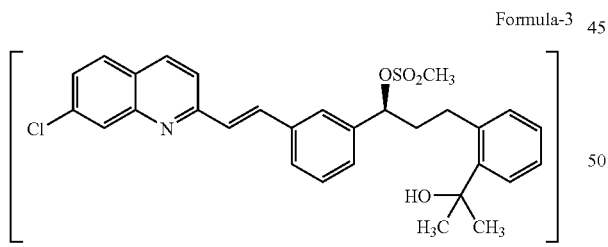

Formula-3

Which on reacting in-situ with pure 1-(mercaptomethyl) cyclopropane acetic acid methyl ester compound of formula-4,

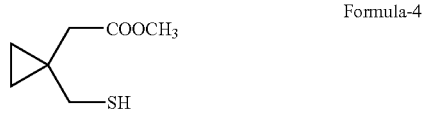

Formula-4 in presence of polar aprotic solvent like dimethylsulfoxide, dimethyl acetamide with or without combination of $C_1$-$C_4$ alcoholic solvents like methanol, ethanol, propanol, butanol, and strong base like alkali or alkaline earth metal alkoxides i.e., potassium tertiary butoxide, sodium methoxide, sodium ethoxide, preferably sodium methoxide in DMSO (dimethylsulfoxide) at a temperature of −20 to 0° C. for 5 to 20 hours, preferably at a temperature of about −5 to 5° C. for 8-10 hours, b) quenching the reaction mixture with an aqueous sodium hydroxide solution, then extracting with water immiscible solvents like hydrocarbon solvents, chloro solvents, ester solvents, preferably hydrocarbon solvents more preferably toluene, c) lowering pH of the reaction mixture with acetic acid then extracting the montelukast with ester solvents, chloro solvents, preferably ester solvents more preferably ethyl acetate followed by concentrating the solvent and then dissolving the obtained residue in a suitable solvent selected from keto solvents like acetone, butanone or ester solvents like ethyl acetate, propyl acetate, preferably acetone and ethyl acetate, d) treating the product obtained from step c. with suitable organic amine such as n-butyl amine, iso-butyl amine (+/−)-sec-butyl amine in a suitable solvent selected from non-polar organic solvents like toluene, cyclohexane, hexane, heptane and/or keto solvents like acetone, butanone, methyl isobutyl ketone and/or ester solvents like ethyl acetate, propyl acetate, preferably non-polar organic solvents more preferably toluene followed by seeding with corresponding organic amine salt of montelukast compound, at a temperature of 20-40° C. for 5-15 hours, preferably at a temperature of about 25-35° C. for 8-10 hours under inert atmosphere to give corresponding amine salt of montelukast compound of formula-5, e) Optionally purifying the corresponding amine salt of montelukast compound of formula-5 using hydrocarbon solvents like toluene, hexanes, heptane or keto solvents like acetone or mixture of them.

The sixth aspect of the present invention is to provide the use of novel organic amine salt of montelukast in the preparation of high pure montelukast or its pharmaceutically acceptable salts for example sodium salt compound of formula-1 in amorphous form,

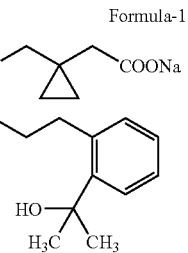

Formula-1

The process for the preparation of amorphous montelukast sodium from the novel organic amine salt of montelukast comprises of treating the organic amine salt of montelukast compound of formula-5 with sodium ion source like sodium hydroxide, sodium methoxide preferably sodium hydroxide in methanol at a temperature of 0-40° C. for 15 to 90 minutes, preferably at a temperature of 5-15° C. for 45 minutes under inert atmosphere, followed by distillation of methanol and organic amine to get the sodium salt of montelukast, which is then dissolved in a suitable solvent like toluene and saturated the toluene layer with a solvent selected from cyclohexane, hexane, heptane preferably heptane, gives montelukast sodium compound of formula-1.

The seventh aspect of the present invention is to provide drying method for amorphous montelukast sodium. Montelukast sodium obtained as per the present invention is dried using tray drier with fan, is placed in HVAC/R (Heating Ventilation Air Conditioning/Refrigeration), which controls the relative humidity (RH) below 40%, to get montelukast sodium having residual solvents well below the ICH limits.

Montelukast sodium prepared as per the prior art processes having residual solvents at the level of nearly equal to the ICH limit even after drying. This limit will not come down further with the known drying techniques. This problem is avoided by the present invention, which is dissolving the montelukast sodium in methanol followed by distillation of methanol followed by drying in rotary drier gives amorphous montelukast sodium having all the residual solvents in not detected level and methanol is about 600 ppm.

Montelukast sodium is a highly hygroscopic compound. Hygroscopy is the ability of a substance to attract water molecules from the surrounding environment through either absorption or adsorption. As montelukast sodium is a highly hygroscopic in nature it should be packed in special manner for stabilization. The process for packing and storage provide herein increased the stability of the amorphous montelukast sodium and increased the shelf life.

A process for packing and storage of amorphous montelukast sodium comprises of the following steps:
a) placing amorphous montelukast sodium in a clear low density polyethylene bag under nitrogen atmosphere tied up with a thread or plastic strip,
b) placing the primary packing containing montelukast sodium inside a black colour low-density polyethylene bag and this bag is tied with a thread or plastic strip,
c) placing the above double polyethylene bag inside a triple laminated bag along with silica gel bag and sealing it,
d) placing the sealed triple laminated bag inside a closed high density polyethylene (HDPE) container.

HPLC analysis of related substances of montelukast sodium is carried out using column symmetry $C_{18}$, 150×3.9 mm ID, 5μ, or equivalent, at a wavelength of 225 nm with gradient flow rate, at 40° C. temperature, load is 20 μl, runtime is 40 minutes, RT of the main peak is at about 16 minutes, the diluent is a mixture of sodiumdihydrogen phosphate (3.9 grams of sodiumdihydrogen phosphate in 1000 ml of water) and acetonitrile in the ratio of 37:63 and using dilute ortho phosphoric acid as a buffer.

HPLC analysis of related substances in [(E)]-2-[3(S)-[3-[2-(7-chloro-2-quinolinyl)ethenyl)phenyl]-3-hydroxypropyl]phenyl]-2-propanol (i.e., corresponding derivatives) is carried out using column symmetry $C_{18}$, 150×3.9 mm ID, 5μ, or equivalent, at a wavelength of 240 nm with a flow rate of 1 ml/min, at 40° C. temperature, load is 20 μl, runtime is 40 minutes, RT of the main peak is at about 10 minutes, the diluent is a sodiumdihydrogen phosphate (3.9 grams of sodiumdihydrogen phosphate in 1000 ml of water) and adjust the pH to 3.7 with dilute ortho phosphoric acid. Mobile phase is acetonitirle:phosphate buffer in the ratio of 63:37 and acetonitrile:water in the ratio of 90:10.

XRD analysis of n-butyl amine salt of montelukast is carried out using SIEMENS/D-5000 X-Ray Diffractometer using Cu, Ka radiation of wavelength 1.54 A° and continuous scan speed of 0.045°/min.

FI-IR spectrum of n-butyl amine salt of montelukast was recorded on Thermo model Nicolet-380 as KBr pellet.

The thermal analysis of n-butyl amine salt of montelukast was carried out on Waters DSC Q-10 model differential scanning calorimeter.

HPLC Analysis of compound of formula-7 is carried out to find out the diacid impurity, using Develosil ODS MG-5 250×4.6 mm×5 μm or equivalent column at a wavelength of 200 nm with isocratic elution, at 27° C. temperature, load is 20 μl, runtime is 60 minutes, the diluent is a mixture of acetonitrile and water at a ratio of 800:200.

HPLC analysis of diacid impurity content in montelukast sodium is carried out using Inertsil ODS-3V 250×4.6 mm×5 μm or equivalent, at a wavelength of 200 nm, at 28° C. temperature, load is 20 μl, runtime is 35 minutes, with the sample concentration is 5 mg/ml; the diluent is a mixture of water and acetonitrile in the ratio of 20:80.

Purity of compound of formula-7 by GC is carried out using a gas chromatograph is equipped with flame ionization detector; Column: AT-Wax or equivalent; Length is 30 mts. ID is 0.25 mm.; Film thickness is 0.25 μm.; Injector temperature is 200° C.; Split is 1:50; Detector temperature at 240° C.; Carrier gas pressure at 19.1 Psi with Injection load of 0.2 μl.

Microscopic analysis of montelukast sodium is analyzed as follows;

The samples are moulded on alumina stubs using double adhesive tape, coated with gold using HUS-5 GB vacuum evaporator and observed in Hitachi S-520 Scanning Electron Microscope at an acculation voltage of 10 KV.

The present invention schematically represented as below

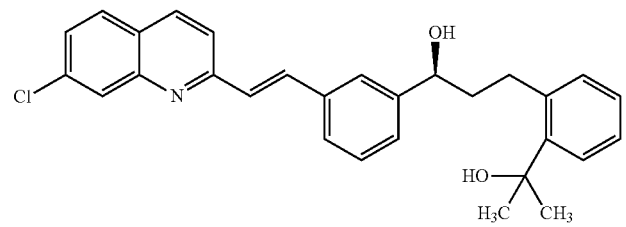

Formula-2

Methanesulfonyl chloride
Toluence/Acetonitrile

-continued
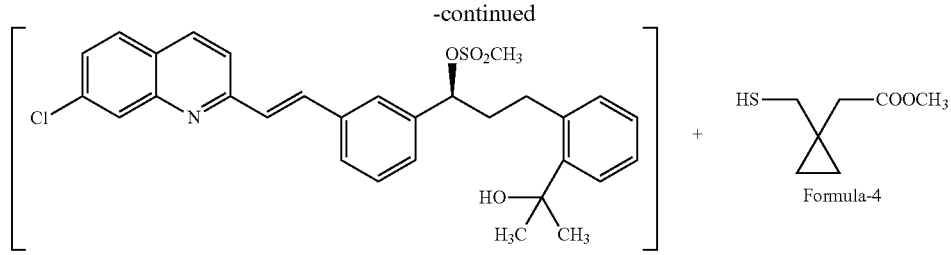
Formula-3    Formula-4
Sodium methoxide
DMSO/Methanol
Organic amine
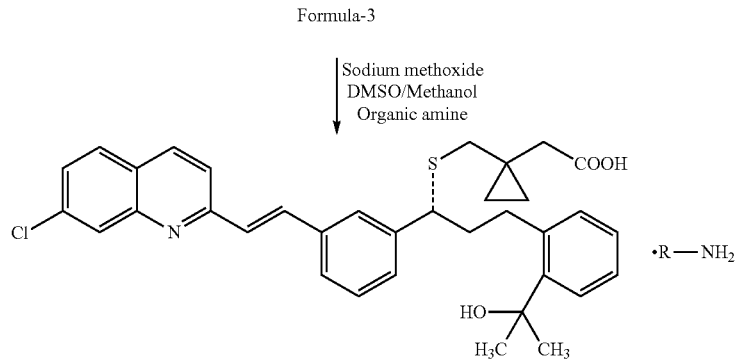
Formula-5
Sodium hydroxide
Methanol
Toluene
Heptane
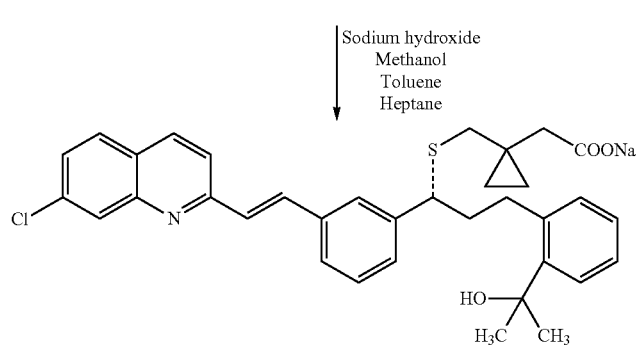
Formula-1
The possible impurities of Montelukast sodium are as follows

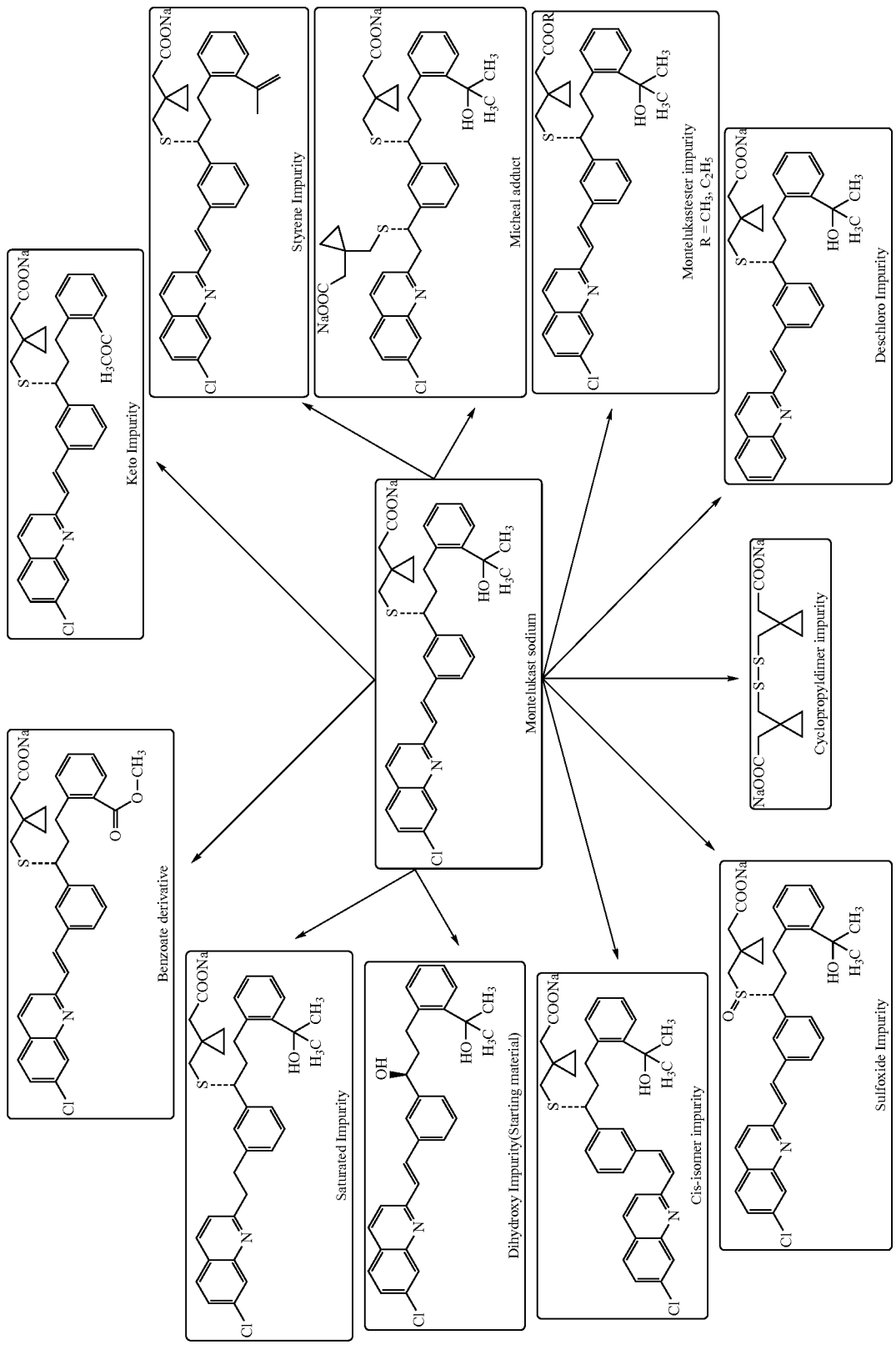

The processes described in the present invention were demonstrated in examples illustrated below. These examples are provided as illustration only and therefore should not be construed as limitation of the scope of the invention.

EXAMPLES

Reference Example-1

A mixture of 8 grams of [(E)]-2-[3(S)-[3-[2-(7-chloro-2-quinolinyl)ethenyl)phenyl]-3-hydroxypropyl]phenyl]-2-propanol, 16 ml of toluene and 71.5 ml of acetonitrile was heated to 40-50° C. Stirred the reaction mixture for 30 minutes at 40-50° C. Cooled the reaction mixture to −20 to −15° C. Added 2.74 grams of diisopropylethylamine slowly to the above reaction mixture at −20 to −15° C. Stirred the reaction mixture for 45 minutes at −20 to −15° C. Added 2.2 grams of methanesulfonylchloride to the above reaction mixture at −20 to −15° C. Stirred the reaction mixture for 10 hours at −20 to −15° C. Filtered the precipitated solid and washed with chilled acetonitrile followed by hexanes to get the wet solid material. Added 3.12 grams of 1-(mercapto methyl)cyclopropane acetic acid methyl ester to the pre cooled mixture of 32 ml of dimethyl sulfoxide and 14.2 ml of sodium methoxide solution at −5 to 0° C. Stirred the reaction mixture for one hour at −5 to 0° C. The above obtained wet solid material added lot wise to the reaction mixture at −5 to 0° C. Stirred the reaction mixture for 10 hours at −5 to 0° C. Added the above reaction mixture to the pre cooled 238 ml of water at below 10° C. Stirred the reaction mixture for 30 minutes. Added 32 ml of toluene to the above reaction mixture at 25-30° C. Adjusted the pH of the reaction mixture to 13.4 with aqueous sodium hydroxide (6.3 grams in 238 ml of water) solution. Stirred the reaction mixture for 30 minutes at 25-30° C. Separated the organic and aqueous phases. Washed the aqueous phase thrice with toluene. Then cooled the aqueous phase to 10-20° C. Adjusted the pH of the reaction mixture to 6.6 with aqueous acetic acid solution. Extracted the reaction mixture thrice with ethyl acetate. Washed the organic phase with aqueous sodium bicarbonate solution. Separated the organic and aqueous phases. Dried the organic phase with sodium sulphate. Distilled the solvent completely under reduced pressure at below 60° C. Cooled the reaction mixture to 25-30° C. Added 32 ml of toluene to the above reaction mixture. Again distilled the solvent completely under reduced pressure at below 60° C.

Reference Example-2

A mixture of 8 grams of [(E)]-2-[3(S)-[3-[2-(7-chloro-2-quinolinyl)ethenyl)phenyl]-3-hydroxypropyl]phenyl]-2-propanol, 16 ml of toluene and 71.5 ml of acetonitrile was heated to 40-50° C. Stirred the reaction mixture for 30 minutes at 40-50° C. Cooled the reaction mixture to −20 to −15° C. Added 2.74 grams of diisopropylethylamine slowly to the above reaction mixture at −20 to −15° C. Stirred the reaction mixture for 45 minutes at −20 to −15° C. Added 2.2 grams of methanesulfonylchloride to the above reaction mixture at −20 to −15° C. Stirred the reaction mixture for 10 hours at −20 to −15° C. Filtered the precipitated solid and washed with chilled acetonitrile followed by hexanes to get the wet solid material. Added 3.12 grams of 1-(mercapto methyl)cyclopropane acetic acid to the pre cooled mixture of 32 ml of dimethyl sulfoxide and 14.2 ml of sodium methoxide solution at −5 to 0° C. Stirred the reaction mixture for 10 hour at −5 to 0° C. Stirred the reaction mixture at −5 to 5° C. for 10 hours. Added the reaction mixture to 238 ml of chilled water at below 10° C. Stirred the reaction mixture at 10-20° C. for 30 minutes. Slowly added sodium hydroxide solution at 10-20° C. Washed the reaction mixture with toluene and removed the toluene layer. Cooled the aqueous layer to 10-20° C. and slowly added 50% acetic acid solution. Extracted the reaction mixture thrice with ethyl acetate. Washed the organic phase with aqueous sodium bicarbonate solution. Separated the organic and aqueous phases. Dried the organic phase with sodium sulphate. Distilled the solvent completely under reduced pressure at below 60° C. Cooled the reaction mixture to 25-30° C. Added 32 ml of toluene to the above reaction mixture. Again distilled the solvent completely under reduced pressure at below 60° C.

Example-1

Preparation of N-Butyl Amine Salt of Montelukast

Added 48 ml of ethyl acetate to the crude obtained as per the example 1 or example-2, followed by 0.9 grams of n-butyl amine at 25-30° C. Seeded with n-butyl amine salt of montelukast. Stirred the reaction mixture for 8 hours at 25-30° C. Filtered the precipitated solid and washed with ethyl acetate. Dried the material at 60-65° C. for 8 hours. Added 32 ml of toluene to the above obtained dried material and heated to 70-80° C. Stirred the reaction mixture for 30 minutes at 70-80° C. Cooled the reaction mixture to 25-35° C. Stirred the reaction mixture for 10 hours at 25-35° C. Filtered the precipitated solid. Dissolved the wet solid in 79 ml of toluene. Heated the reaction mixture to 70-80° C. and stirred the reaction for 30 minutes. Cooled the reaction mixture to 25-30° C. Stirred the reaction for 10 hours at 25-30° C. Filtered the precipitated solid and dried the material at 50-55° C. to get the title compound.

Yield: 5.7 grams.
HPLC Purity: 99.72%

Example-2

Preparation of Isobutyl Amine Salt Montelukast

Added 48 ml of ethyl acetate to the crude obtained as per the example 1 or example-2, followed by 0.9 grams of isobutyl amine at 25-30° C. Seeded with isobutyl amine salt of montelukast. Stirred the reaction mixture for 8 hours at 25-30° C. Filtered the precipitated solid and washed with ethyl acetate. Dried the material at 60-65° C. for 8 hours. Added 32 ml of toluene to the above obtained dried material and heated to 70-80° C. Stirred the reaction mixture for 30 minutes at 70-80° C. Cooled the reaction mixture to 25-35° C. Stirred the reaction mixture for 10 hours at 25-35° C. Filtered the precipitated solid. Dissolved the wet solid in 79 ml of toluene. Heated the reaction mixture to 70-80° C. and stirred the reaction for 30 minutes. Cooled the reaction mixture to 25-30° C. Stirred the reaction for 10 hours at 25-30° C. Filtered the precipitated solid and dried the material at 50-55° C. to get the title compound.

Yield: 5.5 grams.
HPLC Purity: 99.57%

Example-3

Preparation of (+) sec-butyl amine salt montelukast

Added 48 ml of ethyl acetate to the crude obtained as per the example 1 or example-2, followed by 0.9 grams of (+) sec-butyl amine at 25-30° C. Seeded with (+)-sec-butyl amine salt of montelukast. Stirred the reaction mixture for 8 hours at 25-30° C. Filtered the precipitated solid and washed with ethyl acetate. Dried the material at 60-65° C. for 8 hours.

Added 32 ml of toluene to the above obtained dried material and heated to 70-80° C. Stirred the reaction mixture for 30 minutes at 70-80° C. Cooled the reaction mixture to 25-35° C. Stirred the reaction mixture for 10 hours at 25-35° C. Filtered the precipitated solid. Dissolved the wet solid in 79 ml of toluene. Heated the reaction mixture to 70-80° C. and stirred the reaction for 30 minutes. Cooled the reaction mixture to 25-30° C. Stirred the reaction for 10 hours at 25-30° C. Filtered the precipitated solid and dried the material at 50-55° C. to get the pure title compound.

Yield: 5.2 grams
HPLC Purity: 99.27%

Example-4

Preparation of Montelukast Sodium from N-Butylamine Salt of Montelukast

Added methanolic sodium hydroxide solution (0.34 grams in 8.5 ml of methanol) to a pre cooled solution of 5.5 grams of montelukast n-butyl amine compound of formula-1, 16.5 ml of methanol at 5-10° C. Stirred the reaction mixture for 30 minutes at 5-10° C. Distilled the solvent completely under reduced pressure at 55° C. Cooled the reaction mixture to 35-40° C. Added 11 ml of toluene to the above mass and distilled the solvent completely under reduced pressure at below 65° C. The distillation process repeated twice. Cooled the reaction mixture to 25-30° C. Added 33 ml of toluene to the above reaction mixture. Stirred the reaction mixture for 30 minutes. Treated the reaction mixture with 1.65 grams of activated carbon. Stirred the reaction mixture for 20 minutes at 25-30° C. Filtered the reaction mixture through hyflow and washed with toluene. Partially distilled the filtrate under reduced pressure at below 65° C. Cooled the reaction mixture to 35-40° C. The above reaction mixture slowly added to 49.5 grams of heptane at 25-30° C. Stirred the reaction mixture for 4 hours at 25-30° C. Filtered the precipitated solid. Dried the compound at 60-70° C. under reduced pressure to get the title compound.

Yield: 4.4 grams
Montelukast sodium purity by HPLC: 99.72%
Diacid content by HPLC: Not detected, RRT: 0.37
Particle size: D (v, 0.1) is 3.19 μm, D (v, 0.5) is 20.10 μm, D (v, 0.9) is 68.26 μm, D [4,3] is 29.24 μm.

Example-5

Preparation of Montelukast Sodium from Iso-Butylamine Salt of Montelukast

The title compound is prepared as per the process described in example-4 using isobutyl amine salt of montelukast in place of n-butylamine salt of montelukast or as per the process disclosed in WO 2007/069261 using iso-butylamine salt in place of tertiarybutylamine salt of montelukast.

Yield: 4.2 grams
HPLC: 99.48%

Example-6

Preparation of Montelukast Sodium from Sec-Butylamine Salt of Montelukast

The title compound is prepared as per the process described in example-4 using sec-butylamine salt of montelukast in place of n-butylamine salt of montelukast or as per the process disclosed in WO 2007/069261 using sec-butylamine salt in place of tertiarybutylamine salt of montelukasts.

Yield: 4.1 grams
HPLC: 99.30%

Example-7

Preparation of Tertiary Butylamine Salt of Montelukast

A mixture of 8.0 Kgs of [(E)]-2-[3(S)-[3-[2-(7-chloro-2-quinolinyl)ethenyl)phenyl]-3-hydroxypropyl]phenyl]-2-propanol, 16 liters toluene and 71.5 liters acetonitrile is heated to 40-50° C. Stirred the reaction mixture for 30 minutes at 40-50° C. Cooled the reaction mixture to −20 to −15° C. Added 2.74 Kgs of diisopropylethylamine slowly to the above reaction mixture at −20 to −15° C. Stirred the reaction mixture for 45 minutes at −20 to −15° C. Added 2.2 Kgs of methanesulfonylchloride to the above reaction mixture at −20 to −15° C. Stirred the reaction mixture for 10 hours at −20 to −15° C. Filtered the precipitated solid and washed with chilled acetonitrile followed by hexanes to get the wet solid material. Added 3.12 Kgs of 1-(mercapto methyl)cyclopropane acetic acid methyl ester compound of formula-4 to the pre cooled mixture of 32 liters of dimethyl sulfoxide and 14.2 liters of sodium methoxide solution at −5 to 0° C. Stirred the reaction mixture for one hour at −5 to 0° C. The obtained wet solid material added lot wise to the above reaction mixture at −5 to 0° C. Stirred the reaction mixture for 10 hours at −5 to 0° C. Added the above reaction mixture to the pre cooled 238 liters of water at below 10° C. Stirred the reaction mixture for 30 minutes. Added 32 liters of toluene to the above reaction mixture at 25-30° C. Adjusted the pH of the reaction mixture to 13.4 with aqueous sodium hydroxide (6.3 Kgs in 238 liters of water) solution. Stirred the reaction mixture for 30 minutes at 25-30° C. Separated the organic and aqueous phases. Washed the aqueous phase thrice with toluene. Then cooled the aqueous phase to 10-20° C. Adjusted the pH of the reaction mixture to 6.6 with aqueous acetic acid solution. Extracted the reaction mixture thrice with ethyl acetate. Washed the organic phase with aqueous sodium bicarbonate solution. Separated the organic and aqueous phases. Dried the organic phase with sodium sulphate. Distilled the solvent completely under reduced pressure at below 60° C. Cooled the reaction mixture to 25-30° C. Added 32 liters of toluene to the above reaction mixture. Again distilled the solvent completely under reduced pressure at below 60° C. Cooled the reaction mixture to 25-30° C. Added 48 liters of ethyl acetate to the above reaction mixture followed by 0.9 Kgs. of tertiarybutylamine at 25-30° C. Stirred the reaction mixture for 8 hours at 25-30° C. Filtered the precipitated solid and washed with ethyl acetate. Dried the material at 60-65° C. for 8 hours. Added 32 liters of toluene to the above obtained dried material and heated to 70-80° C. Stirred the reaction mixture for 30 minutes at 70-80° C. Cooled the reaction mixture to 25-35° C. Stirred the reaction mixture for 10 hours at 25-35° C. Filtered the precipitated solid. Dissolved the wet solid in 79 liters of toluene. Heated the reaction mixture to 70-80° C. and stirred the reaction for 30 minutes. Cooled the reaction mixture to 25-30° C. Stirred the reaction for 10 hours at 25-30° C. Filtered the precipitated solid and dried the material at 50-55° C. to get the pure title compound.

Yield: 5.7 Kgs.
HPLC Purity: 99.67%
Impurity A: 0.1%

Example-8

Preparation of Montelukast Sodium from Tertiary Butylamine Salt of Montelukast

Added Methanolic sodium hydroxide solution (0.34 Kgs in 8.5 liters of methanol) to a pre cooled solution of 5.5 Kgs Montelukast tertiarybutylamine compound of formula-5, 16.5 liters of methanol at 5-10° C. Stirred the reaction mixture for 30 minutes at 5-10° C. Distilled the solvent completely under reduced pressure at 55° C. Cooled the reaction mixture to 35-40° C. Added 11 liters of toluene to the above mass and distilled the solvent completely under reduced pressure at below 65° C. The distillation process repeated twice. Cooled the reaction mixture to 25-30° C. Added 33 liters of toluene to the above reaction mixture. Stirred the reaction mixture for 30 minutes. Treated the reaction mixture with 1.65 Kgs. of activated carbon. Stirred the reaction mixture for 20 minutes at 25-30° C. Filtered the reaction mixture through hyflow and washed with toluene. Distilled the filtrate completely under reduced pressure at below 65° C. Cooled the reaction mixture to 35-40° C. Added slowly the above reaction mixture to the 49.5 liters of heptanes at 25-30° C. Stirred the reaction mixture for 4 hours at 25-30° C. Filtered the precipitated solid. The obtained wet material taken into RCVD (Roto Cone Vccum Drier) and added 2.1 lit. of methanol, applied vacuum to the RCVD at below 40° C. and dried for 4 hours. Temperature of the RCVD raised to 40-50° C. and dried for 6 hours under reduced pressure and further raised the temperature to 55-65° C. and dried for 8 hours. Unloaded the solid to get the highly pure title compound of formula-1.

Yield: 4.4 Kgs.
HPLC: 99.72%
Impurity A: 0.1%; Impurity B: 0.01%; Impurity C: Not detected
Impurity D: Not detected Impurity E: 0.04%;
Styrene impurity: 0.1%;
Cis-isomer impurity: 0.08%
Diacid impurity: Not detected Example-9

Preparation of [(E)-2-[3(S)-[3-[2-(7-chloro-2-quinolinyl)ethenyl]phenyl]-3-hydroxypropyl]phenyl]-2-propanol compound of formula-2

Added a mixture of 150 Kgs. of 2-3 molar solution of methyl magnesium chloride in tetrahydrofuran and 60 liters methylene chloride slowly to a pre cooled solution of 30 Kgs. of methyl2-((S)-3-(3-((E)-2-(7-chloroquinolin-2-yl)phenyl)-3-hydroxypropyl) benzoate compound in 360 liters of methylenechloride at −5 to 5° C. Stirred the reaction mixture for 4 hours. Quenched the above reaction mixture with chilled aqueous acetic acid solution (36 liters in 360 liters of water) at below 15° C. Stirred the reaction mixture for 20 minutes at 25-30° C. Separated the organic and aqueous phases. Extracted the aqueous phase with methylene chloride. Washed the organic phase washed with water followed by sodium bicarbonate solution. Organic phase distilled completely at below 60° C. Added 30 liters of toluene to the above reaction mixture and again distilled the solvent completely under reduced pressure at below 70° C. Added 240 liters of methylene chloride to the above reaction mixture then cooled to −5 to 5° C. Added a mixture of 60 Kgs methyl magnesium chloride and 30 liters methylene chloride is slowly to the above reaction mixture at −5 to 5° C. Stirred the reaction mixture for 1.5 hour at 2 to 6° C. Cooled the reaction mixture to −5 to 5° C. Quenched the above reaction mixture with chilled aqueous acetic acid solution (24 liters in 240 liters of water) at below 15° C. Stirred the reaction mixture for 30 minutes. Separated the organic and aqueous phases. Extracted the aqueous phase with methylene chloride. Organic phase washed with water followed by washed with aqueous sodium bicarbonate solution and water. Organic phase distilled completely under reduced pressure at below 60° C. Added 30 liters of toluene to the above reaction mixture and distilled solvent completely under reduced pressure at below 70° C. Added 30 liters of toluene at 40-45° C. Stirred the reaction mixture for 4 hours at 25-35° C. Added 30 liters of toluene to the above reaction mixture. Heated the reaction mixture to 45-50° C. to make a clear solution. Cooled to 25-35° C. Stirred the reaction mixture for 8 hours at 25-35° C. Added 30 liters of hexanes. Filtered the precipitated solid and washed with mixture of toluene and hexanes solution. Dried the material at 60-65° C. to get the title compound of formula-2.

Yield: 19.5 Kgs.
Purity by HPLC: 98.10%

Example-10

Purification of [(E)]-2-[3(S)-[3-[2-(7-chloro-2-quinolinyl)ethenyl]phenyl]-3-hydroxypropyl]phenyl]-2-propanol compound of formula-2

Heated a mixture of 20 Kgs of compound of formula-2 and 70 liters of toluene to 70-80° C. Stirred the reaction mixture at 70-80° C. up to clear solution. Cooled the reaction mixture to 25-30° C. Stirred the reaction mixture for 10 hours at 25-30° C. Added 20 liters of hexanes to the above reaction mixture and stirred for 45 minutes at 25-30° C. Filtered the precipitated solid and washed with a mixture of toluene and hexanes. Dried the material at 50-60° C. to get the highly pure compound of formula-2

Yield: 18 Kgs.
HPLC purity: 99.84%
Impurity A*, B*, C* and D* are <0.1%.

Example-11

Purification of mercaptomethyl cyclopropane acetic acid compound of formula-7

Mercaptomethyl cyclopropane acetic acid (10 Kgs.) compound of formula-7 having 13% diacid impurity was dissolved in 50 liters of toluene and stirred for 30 minutes at 25-35° C. Cooled the reaction mixture to 0-5° C. Stirred the reaction mixture at 0-5° C. Filtered the precipitated diacid impurity and washed with toluene. Distilled the filtrate completely under reduced pressure at below 55° C. to get the pure compound of formula-7.

Yield: 8.5 Kgs.
G.C, 96.6%.
Diacid content by HPLC: 4.93% RRT: 2.15

Example-12

Drying Method for Montelukast Sodium

Montelukast sodium (2 Kgs. wet material) prepared as per the process exemplified in example-4 was taken in a tray which is placed in tray drier. The tray drier was placed in a room having HVAC/R (Heating Ventilation Air Conditioning/Refrigeration), which controls the relative humidity (RH) below 40%. The material was dried at 90-110° C. for 14 hours to give amorphous montelukast sodium.

Yield: 1.2 Kgs.
RS/OVI result: Toluene: 450 ppm; Heptane: 2200 ppm.

Example-13

Drying Method for Montelukast Sodium

Montelukast sodium (50 grams) having residual solvents toluene 600-890 ppm, heptane 3000-5000 ppm, obtained as per the conventional methods, was dissolved in methanol.

The obtained solution was taken in a Buchi flask and distilled the solvent completely. Dried the material at 90-110° C. in buchi flask for 14 hours to give amorphous montelukast sodium.

Yield: 38 grams

RS/OVI result: Toluene: 50 ppm; Heptane: Not detected

We claim:
1. A process for the preparation of a crystalline form of a compound represented by Formula-5:

Formula-5

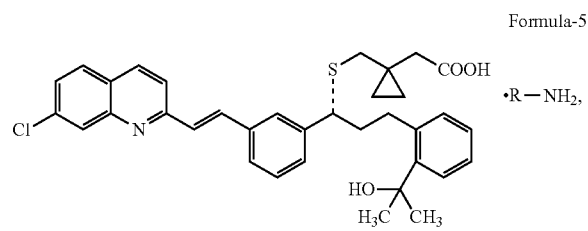

·R—NH$_2$, wherein R is n-butyl and wherein the crystalline form is characterized by x-ray powder diffraction peaks at about 6.2, 8.6, 8.9, 15.0, 16.9, 18.9, 20.7, 22.6, 25.5 and 29.9 degrees two-theta ±0.2 degrees two-theta, the process comprising:
a) reacting a compound represented by Formula-2, Formula-2

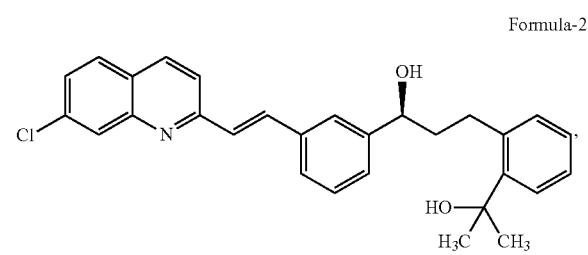

with methane sulfonyl chloride in a solvent or mixture of solvents in the presence of an organic amine base to give a compound represented by Formula-3:

Formula-3

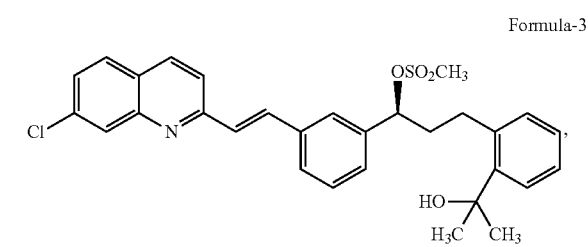

then reacting in-situ the compound represented by Formula-3 with a compound represented by Formula-4:

Formula-4

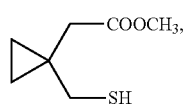

in the presence of a polar aprotic solvent, optionally a $C_1$-$C_4$ alcoholic solvent, and an alkali or alkaline earth metal alkoxide to give montelukast;
b) quenching the reaction mixture with aqueous alkali solution, then extracting the reaction mixture with a water-immiscible solvent;
c) lowering pH of the reaction mixture with an organic acid, then extracting montelukast with ester solvents and chloro solvents, followed by concentrating the solvent and then dissolving the obtained residue in a suitable solvent selected from keto solvents and ester solvents;
d) treating the product obtained from step c) with n-butyl amine in a non-polar organic solvent, keto solvent or ester solvent or a mixture thereof under an inert atmosphere to give a crystalline form of the compound represented by Formula-5; and
e) optionally purifying the crystalline form of a compound represented by Formula-5 using a hydrocarbon solvent or keto solvent or mixture thereof.

2. The process of claim 1, wherein
in step a), the solvent is a mixture of toluene and acetonitrile; the organic amine base is diisopropylethylamine; the polar aprotic solvent is dimethylsulfoxide or dimethyl acetamide; the alcoholic solvent is methanol, ethanol, propanol, or butanol; or the alkali or alkaline earth metal alkoxide is potassium tertiary butoxide, sodium methoxide, or sodium ethoxide; or step a) is conducted at a temperature of −20° C. to 0° C. for 5 to 20 hours; or
in step b), the alkali solution is sodium hydroxide or potassium hydroxide; or the water-immiscible solvent is selected from the group consisting of hydrocarbon solvents, chloro solvents, and ester solvents; or
in step c), the organic acid is acetic acid; the chloro solvent is methylene chloride or chloroform; the ester solvent is ethyl acetate, methyl acetate, or propyl acetate; or the keto solvent is acetone, methyl isobutylketone, or butanone; or
in step d), the non-polar organic solvent is selected from toluene, cyclohexane, hexane and heptane; the ester solvent is selected from ethyl acetate, methyl acetate, or propyl acetate; or the keto solvent is acetone or butanone; or step d) is conducted at a temperature of 20-40° C. for 5-15 hours; or
in step e), the hydrocarbon solvent is toluene, hexanes, or heptanes; or the keto solvent is acetone, butanone, or methyl isobutylketone.

3. The process of claim 1, wherein the compound of Formula-5 has an HPLC purity of at least about 99.5%.

4. The process of claim 1, further comprising:
a) reacting a compound of Formula-6

Formula-6

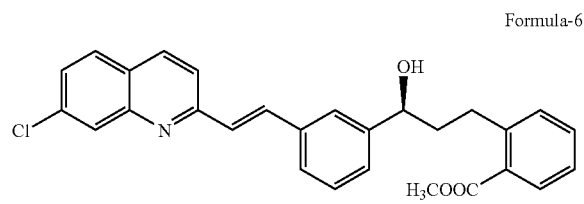

with a Grignard reagent in an organic solvent in combination with a co-solvent to give the compound of Formula-2; and
b) purifying the compound of Formula-2 in a hydrocarbon solvent to give the compound of Formula-2 free from the compounds represented by the following structural formulas:

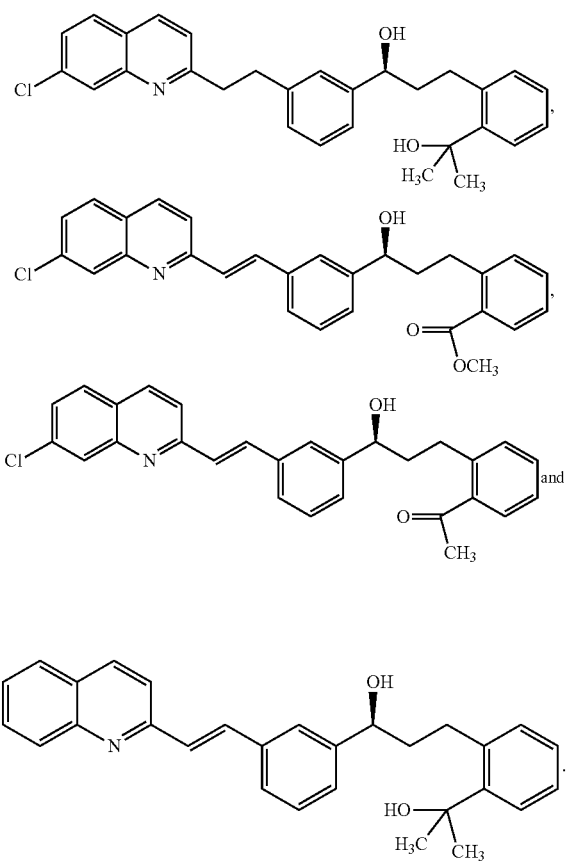

5. The process of claim 4, wherein:
in step a), the Grignard reagent is methyl magnesium chloride or methyl magnesium bromide; the organic solvent is toluene or tetrahydrofuran; or the co-solvent is methylene chloride; or
in step b), the hydrocarbon solvent is toluene, cyclohexane, heptane, or hexane.

6. A crystalline form of a compound represented by Formula-5:

Formula-5

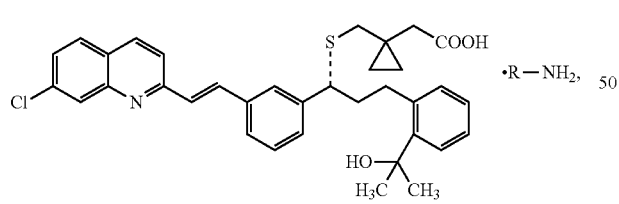

wherein R is n-butyl and wherein the crystalline form is characterized by x-ray powder diffraction peaks at about 6.2, 8.6, 8.9, 15.0, 16.9, 18.9, 20.7, 22.6, 25.5 and 29.9 degrees two-theta ±0.2 degrees two-theta.

7. A process for the preparation of an amorphous form of a compound represented by Formula-1 from a crystalline form of a compound represented by Formula-5, the process comprising:
a) treating the crystalline form of a compound of Formula-5

Formula-5

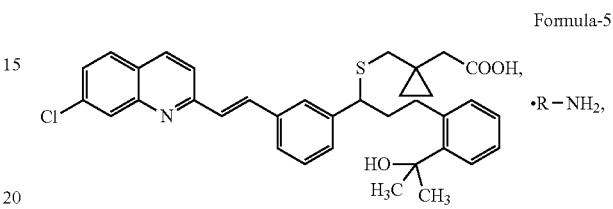

wherein R is n-butyl and wherein the crystalline form is characterized by x-ray powder diffraction peaks at about 6.2, 8.6, 8.9, 15.0, 16.9, 18.9, 20.7, 22.6, 25.5 and 29.9 degrees two-theta ±0.2 degrees two-theta,
with a sodium ion source in methanol under an inert atmosphere;
b) distilling the methanol and the n-butyl amine to get the compound represented by Formula-1:

Formula-1

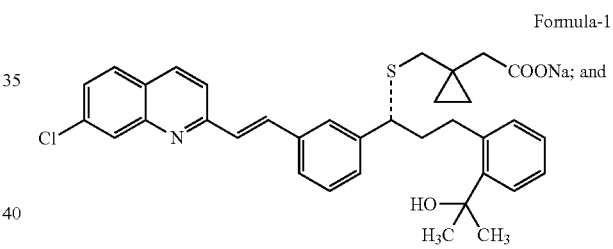

c) dissolving the compound represented by Formula-1 in toluene and saturating the toluene with a solvent selected from cyclohexane, hexane and heptanes, thereby preparing an amorphous form of a compound represented by Formula-1.

8. The process of claim 7, wherein:
in step a), the sodium ion source is sodium hydroxide or sodium methoxide; or step a) is conducted at a temperature of 0-40° C. for 15 to 90 minutes; or
in step c), the solvent is heptanes.

* * * * *

UNITED STATES PATENT AND TRADEMARK OFFICE
CERTIFICATE OF CORRECTION

PATENT NO. : 8,115,004 B2  
APPLICATION NO. : 12/312660  
DATED : February 14, 2012  
INVENTOR(S) : Manne Satyanarayana Reddy et al.

Figure 5:
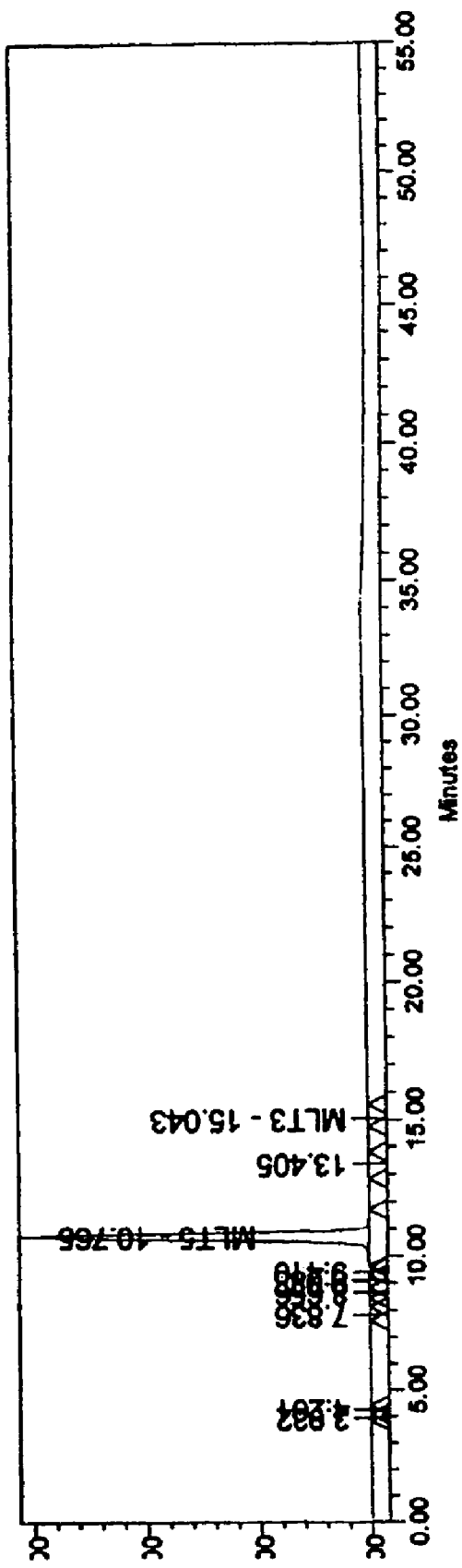
FIG. 5: Illustrates the HPLC chromatogram of compound of formula-2 after purification.
Figure 6:
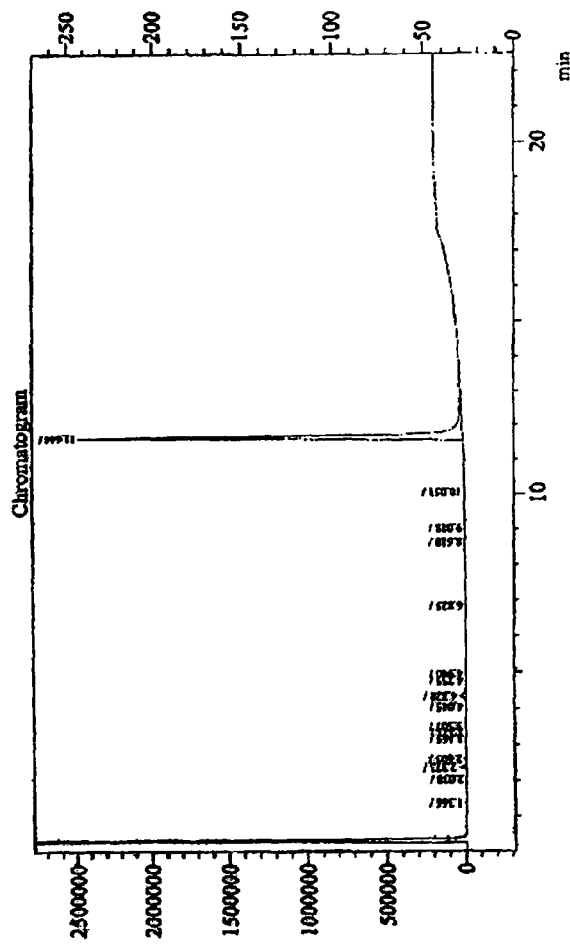
FIG. 6: Illustrates the morphology of montelukast sodium as seen through microscope.

It is certified that error appears in the above-identified patent and that said Letters Patent is hereby corrected as shown below:

In Column 10, line 39, delete "FIG. 5" and insert --FIG. 6--

Figure 7:
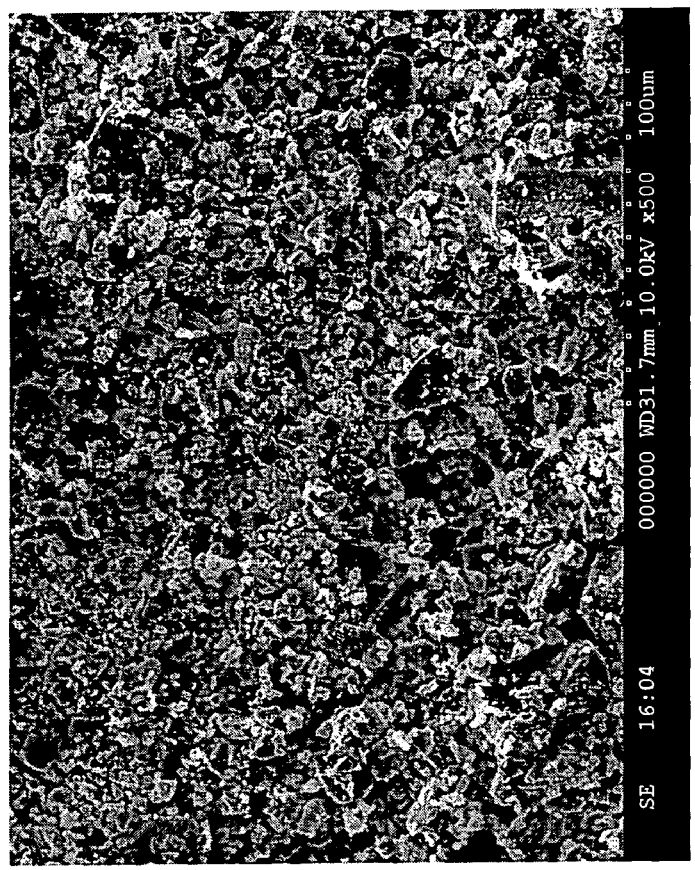
Figure 7:
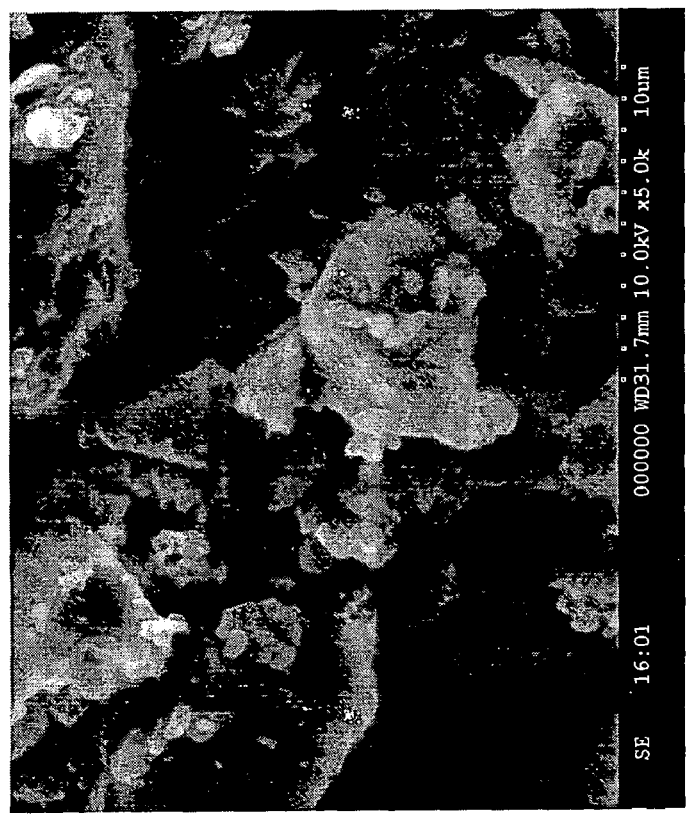

In Column 10, line 41, delete "FIG. 6" and insert --FIG. 7--

In Column 24, line 19, delete "the example" and insert --the reference example--

In Column 24, line 41, delete "the example" and insert --the reference example--

In Column 24, line 63, delete "the example" and insert --the reference example--

In Column 25, line 20, delete "compound of formula-1" and insert --compound obtained from Example-1--

In Column 27, line 1, delete "of formula-5"

In Column 32, Claim 7, lines 15-20, delete Formula-5 and replace with the following formula:

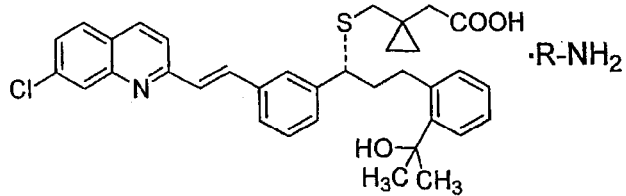

Signed and Sealed this
Seventh Day of August, 2012

David J. Kappos  
*Director of the United States Patent and Trademark Office*